US008606591B2

(12) United States Patent
Heniford et al.

(10) Patent No.: US 8,606,591 B2
(45) Date of Patent: Dec. 10, 2013

(54) SYSTEMS, METHODS, AND COMPUTER PROGRAM PRODUCTS FOR DETERMINING AN OPTIMUM HERNIA REPAIR PROCEDURE

(75) Inventors: Brant Todd Heniford, Charlotte, NC (US); Amy Elizabeth Lincourt, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 842 days.

(21) Appl. No.: 11/937,837

(22) Filed: Nov. 9, 2007

(65) Prior Publication Data

US 2008/0114617 A1      May 15, 2008

Related U.S. Application Data

(60) Provisional application No. 60/865,206, filed on Nov. 10, 2006.

(51) Int. Cl.
  *G06Q 10/00*      (2012.01)
  *G06Q 50/00*      (2012.01)

(52) U.S. Cl.
  USPC .................................................. 705/2; 705/3

(58) Field of Classification Search
  USPC .................................................. 705/2, 3, 2.3
  See application file for complete search history.

(56) References Cited

U.S. PATENT DOCUMENTS

| | | |
|---|---|---|
| 2002/0019747 A1 | 2/2002 | Ware et al. |
| 2002/0035486 A1 | 3/2002 | Huyn et al. |
| 2005/0080462 A1 | 4/2005 | Jenkins et al. |
| 2005/0203773 A1* | 9/2005 | Soto et al. ........................ 705/2 |
| 2005/0273359 A1* | 12/2005 | Young ............................... 705/2 |
| 2008/0040151 A1* | 2/2008 | Moore ............................... 705/2 |
| 2008/0109252 A1* | 5/2008 | LaFountain et al. ............... 705/2 |
| 2008/0270175 A1* | 10/2008 | Rodriguez et al. ................. 705/2 |

FOREIGN PATENT DOCUMENTS

WO      WO 03/104939 A2      12/2003

OTHER PUBLICATIONS http://www.springerlink.com/content/q5x5638290tm5811/fulltext.pdf.*
http://jpubhealth.oxfordjournals.org/content/18/1/49.full.pdf.*
Your Health and Well-Being (SF-36), SF-36v2™ Health Survey © 1996, 2000 by QualityMetric Incorporated and Medical Outcomes Trust.

* cited by examiner

*Primary Examiner* — Robert Morgan
*Assistant Examiner* — Maroun Kanaan
(74) *Attorney, Agent, or Firm* — Alston & Bird LLP

(57) ABSTRACT

Systems, methods, and computer program products are provided for determining an optimum hernia repair procedure for a pre-operative patient. Responses to a health questionnaire administered to post-operative patients are scored to determine an overall score indicative of the post-operative patient's quality of life following a hernia repair procedure. Each overall score is associated with at least one patient characteristic and one procedure characteristic relating to the respective post-operative patient. Based on the overall scores and the associated characteristics, an optimum hernia repair procedure, including a type of operation and/or a type of prosthetic mesh, is determined. A terminal and/or user input device may be used to receive the responses, and the responses and associated characteristics may be stored in a memory accessible by a processor that can analyze the stored data to make the determination. Search criteria relating to the pre-operative patient may also be received to inform the analysis.

25 Claims, 11 Drawing Sheets

CS Questionnaire (All Mesh Types)

CS Questionnaire (All Mesh Types)

SF-36® Questionnaire (All Mesh Types)

CS Questionnaire (Marlex® Mesh Only)

SF-36® Questionnaire (Marlex® Mesh Only)

CS Questionnaire (DualPlus® Mesh Only)

SF-36® Questionnaire (DualPlus® Mesh Only)

SYSTEMS, METHODS, AND COMPUTER PROGRAM PRODUCTS FOR DETERMINING AN OPTIMUM HERNIA REPAIR PROCEDURE

CROSS-REFERENCE TO RELATED APPLICATIONS

This application claims the benefit of U.S. Provisional Application No. 60/865,206, filed Nov. 10, 2006.

BACKGROUND OF THE INVENTION

Prosthetic mesh products have radically changed the repair of all types of hernias. The benefits of mesh repairs have been clearly established in clinical practice, with recurrence rates significantly lower compared to repairs performed without mesh reinforcement. The search for an ideal mesh, however, is ongoing. The characteristics of an ideal prosthetic would include being chemically inert, resistant to mechanical stress, resistant to infections, pliable, and less likely to provoke inflammation and foreign material reactions. Although a wide variety of prosthetic meshes have been used in surgical procedures, no single prosthetic mesh has yet been able to achieve all of the above-identified characteristics.

The long-term implantation of prosthetic mesh is often associated with decreased abdominal wall compliance. Many prosthetics, although chemically inert, generate an intense inflammatory reaction. The result is a pronounced perifilamentous fibrosis and deposition of collagen fibers producing a rigid scar plate and prosthetic mesh "stiffness." In the long-term, such acquired stiffness of mesh products contributes to abdominal wall rigidity, leading to the changes in compliance of both the hernia site and the whole abdominal wall. Clinically, this decrease in compliance can lead to a sensation of firmness of the abdominal wall and result in physical discomfort and significant limitations in the activities of daily living in many patients. Additionally, areas of the abdominal wall that lack prosthetic mesh coverage may experience an increase in herniation as the abdominal pressures are no longer distributed evenly.

Although the clinical benefits of prosthetic mesh repairs have been well established, the effects of prosthetic meshes on patients' quality of life and physical comfort are not well known. Quality of life in hernia patients have traditionally been measured with generic quality of life surveys such as the Rand 36-Item Health Survey (SF-36® questionnaire, Medical Outcomes Trust, Inc, Boston, Mass.). Although this survey has been validated by numerous studies, it doesn't relate specifically to problems/concerns patients have after undergoing hernia repairs with prosthetic mesh. As a result, the ability to identify prosthetic meshes and techniques that most closely meet the desirable characteristics of an ideal hernia repair has been limited.

Thus, there still exists a need for a method of identifying a hernia repair procedure that will have a smaller impact on a particular patient's quality of life.

BRIEF SUMMARY OF THE INVENTION

The present invention provides systems, computer program products, and methods for determining a hernia repair procedure for a pre-operative patient. In general, a short, disease-specific quality of life questionnaire (such as a comfort scale questionnaire) is administered to a number of patients who have undergone a hernia repair procedure. In particular, the questionnaire is directed to the severity of symptoms experienced by the post-operative patient related to various aspects of the patient's quality of life. The responses collected from the post-operative patients are scored and associated with procedure characteristic and patient characteristics. The data is then statistically analyzed to determine an optimum hernia repair procedure for a pre-operative patient having certain characteristics based on the scores and associated characteristics of the collected responses.

In one embodiment, a system for determining a hernia repair procedure for a pre-operative patient is provided that includes a user input device, a memory configured to store data, and a processor in communication with the user input device and memory that is configured to execute various program modules. The user input device is configured to receive a response to a health questionnaire administered to a patient who has previously undergone a hernia repair procedure in which a prosthetic mesh was used to repair the hernia. The health questionnaire includes a plurality of questions, and each question relates to the effect of the hernia repair procedure on an aspect of the post-operative patient's quality of life including severity of pain, sensations of the prosthetic mesh, and limitations in movement experienced by the post-operative patient in connection with performing at least five activities such as lying down, bending over, sitting up, walking, exercising, walking up stairs, performing activities of daily life, coughing, and deep breathing.

The processor may be configured to execute a first program module operable for scoring the response to determine an overall score indicative of the respective post-operative patient's quality of life. A second program module, also executable by the processor, may associate the overall score with at least one characteristic of the respective post-operative patient and with at least one characteristic of the respective hernia repair procedure performed. Furthermore, a third program module may determine an optimum hernia repair procedure for the pre-operative patient based on the overall score and the associated patient characteristics.

In some cases, the user input device is configured to receive a rating as an answer to each question. The rating may be indicative of the effect of the associated hernia repair procedure on the aspect of the post-operative patient's quality of life included in the respective question, and the overall score may be a sum of the ratings. The user input device may also be configured to receive at least one patient characteristic relating to the post-operative patient including the patient's age, gender, type of hernia, and pre-operative health and to receive at least one procedure characteristic relating to the post-operative patient selected from the group consisting of the type of operation performed and the type of prosthetic mesh used in the procedure. Furthermore, the user input device may be configured to receive at least one characteristic relating to the pre-operative patient including the pre-operative patient's age, gender, type of hernia, pre-operative health, and type of operation recommended.

The memory may be configured to store a number of responses and associated patient and procedure characteristics relating to various post-operative patients. In some cases, the processor may be configured to access the responses and associated characteristics from the memory, to analyze any response having at least one associated characteristic that matches a characteristic of the pre-operative patient, and to select the hernia repair procedure associated with the most matching responses having an overall score indicating the least effect of the hernia repair procedure on the respective post-operative patient's quality of life. In other cases, the processor is configured to access the responses and associated characteristics from the memory, to identify at least one of the responses that has the greatest number of associated patient characteristics that match characteristics of the pre-operative patient, and to select the hernia repair procedure associated with the most identified responses having an overall score indicating the least effect of the hernia repair procedure on the respective post-operative patient's quality of life. Furthermore, the system may include a display device configured to present the health questionnaire to a user.

In other embodiments, a system for determining a hernia repair procedure for a pre-operative patient is provided that includes a database of responses to a health questionnaire, a terminal, and a server in communication with the database and the terminal. The health questionnaire is administered to patients who have previously undergone a hernia repair procedure in which a prosthetic mesh was used to repair the hernia, and each response is associated with an overall score indicative of the effect of the hernia repair procedure on an aspect of the post-operative patient's quality of life including severity of pain, sensations of the prosthetic mesh, and limitations in movement experienced by the post-operative patient in connection with performing at least five activities. The five activities may include lying down; bending over, sitting up, walking, exercising, walking up stairs, performing activities of daily life, coughing, and deep breathing. Furthermore, each overall score is associated with at least one characteristic of the respective post-operative patient and with at least one characteristic of the respective hernia repair procedure performed.

The terminal is configured to receive search criteria including at least one characteristic relating to the pre-operative patient, which may include the pre-operative patient's age, gender, type of hernia, pre-operative health, and type of operation recommended. The server is configured to query the database and to determine an optimum hernia repair procedure for the pre-operative patient based on the overall scores, the associated patient characteristics, and the search criteria received.

In some cases, the server is configured to analyze the responses in the database having at least one associated patient characteristic that matches at least one characteristic included in the search criteria and to select the hernia repair procedure associated with the most matching responses having an overall score indicating the least effect of the hernia repair procedure on the respective post-operative patient's quality of life. Alternatively, the server may be configured to identify at least one of the responses in the database that has the greatest number of associated characteristics that match the search criteria and to select the hernia repair procedure associated with the identified responses having an overall score indicating the least effect of the hernia repair procedure on the respective post-operative patient's quality of life.

In some embodiments, a method and computer program product are provided for determining a hernia repair procedure for a pre-operative patient. The method and computer program product receive a number of responses to health questionnaires administered to patients who have previously undergone a hernia repair procedure in which a prosthetic mesh was used to repair the hernia. Each health questionnaire includes a number of questions, and each question relates to the effect of the hernia repair procedure on an aspect of the post-operative patient's quality of life including severity of pain, sensations of the prosthetic mesh, and limitations in movement experienced by the patient in connection with performing at least five activities including lying down, bending over, sitting up, walking, exercising, walking up stairs, performing activities of daily life, coughing, and deep breathing. Each response is scored to determine an overall score indicative of a post-operative quality of life for each respective post-operative patient, and each overall score is associated with at least one characteristic of the respective post-operative patient and with at least one characteristic of the respective hernia repair procedure performed. An optimum hernia repair procedure for the pre-operative patient is then determined based on the overall scores and the associated characteristics.

A rating may be received as an answer to each question in some cases, where the rating is indicative of the effect of the associated hernia repair procedure on an aspect of the post-operative patient's quality of life included in the respective question. Scoring each response in these cases may thus include adding the ratings. Furthermore, at least one patient characteristic that relates to the post-operative patient and at least one procedure characteristic relating to the post-operative patient may be received. The patient characteristic may include the patient's age, gender, type of hernia, and pre-operative health, and the procedure characteristic may include the type of operation performed and the type of prosthetic mesh used in the procedure. In some cases, at least one characteristic relating to the pre-operative patient may be received, such as the pre-operative patient's age, gender, type of hernia, pre-operative health, and type of operation recommended.

In some cases, an optimum hernia repair procedure for the pre-operative patient may be determined by analyzing responses having at least one associated characteristic that matches a characteristic of the pre-operative patient and selecting the hernia repair procedure associated with the most matching responses having an overall score indicating the least effect of the hernia repair procedure on the respective post-operative patient's quality of life. In other cases, an optimum hernia repair procedure for the pre-operative patient may be determined by identifying at least one of the responses that has the greatest number of associated patient characteristics that match patient characteristics of the pre-operative patient and selecting the hernia repair procedure associated with the identified responses having an overall score indicating the least effect of the hernia repair procedure on the respective post-operative patient's quality of life.

Other embodiments provide a method and computer program product for determining a hernia repair procedure for a pre-operative patient. At least one characteristic relating to the pre-operative patient, which may include the pre-operative patient's age, gender, type of hernia, pre-operative health, and type of operation recommended, is provided as a search criteria to a computer system. A database of responses to health questionnaires is then queried to identify responses matching at least one of the search criteria provided, where the health questionnaires were administered to a plurality of patients who have previously undergone a hernia repair procedure in which a prosthetic mesh was used to repair the hernia, and where each health questionnaire includes a number of questions that relate to the effect of the hernia repair procedure on an aspect of the post-operative patient's quality of life, such as severity of pain, sensations of the prosthetic mesh, and limitations in movement experienced by the post-operative patient in connection with performing at least five activities that may include lying down, bending over, sitting up, walking, exercising, walking up stairs, performing activities of daily life, coughing, and deep breathing.

At least one output may then be received, including an optimum type of operation and/or an optimum type of prosthetic mesh to be used in the hernia repair procedure for the pre-operative patient. The output may be based on an analysis of the identified responses, where the analysis determines the output having the least effect on a post-operative patient having the greatest number of characteristics in common with the pre-operative patient. In some cases, multiple characteristics relating to the pre-operative patient may be prioritized such that identified responses matching characteristics having the highest priority are considered more significant than identified responses matching characteristics having priorities less than the highest priority.

Thus, embodiments of the present invention use responses to a disease-specific quality of life questionnaire to a hernia repair procedure for a pre-operative patient that is more likely to have the smallest effect on the patient's quality of life.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
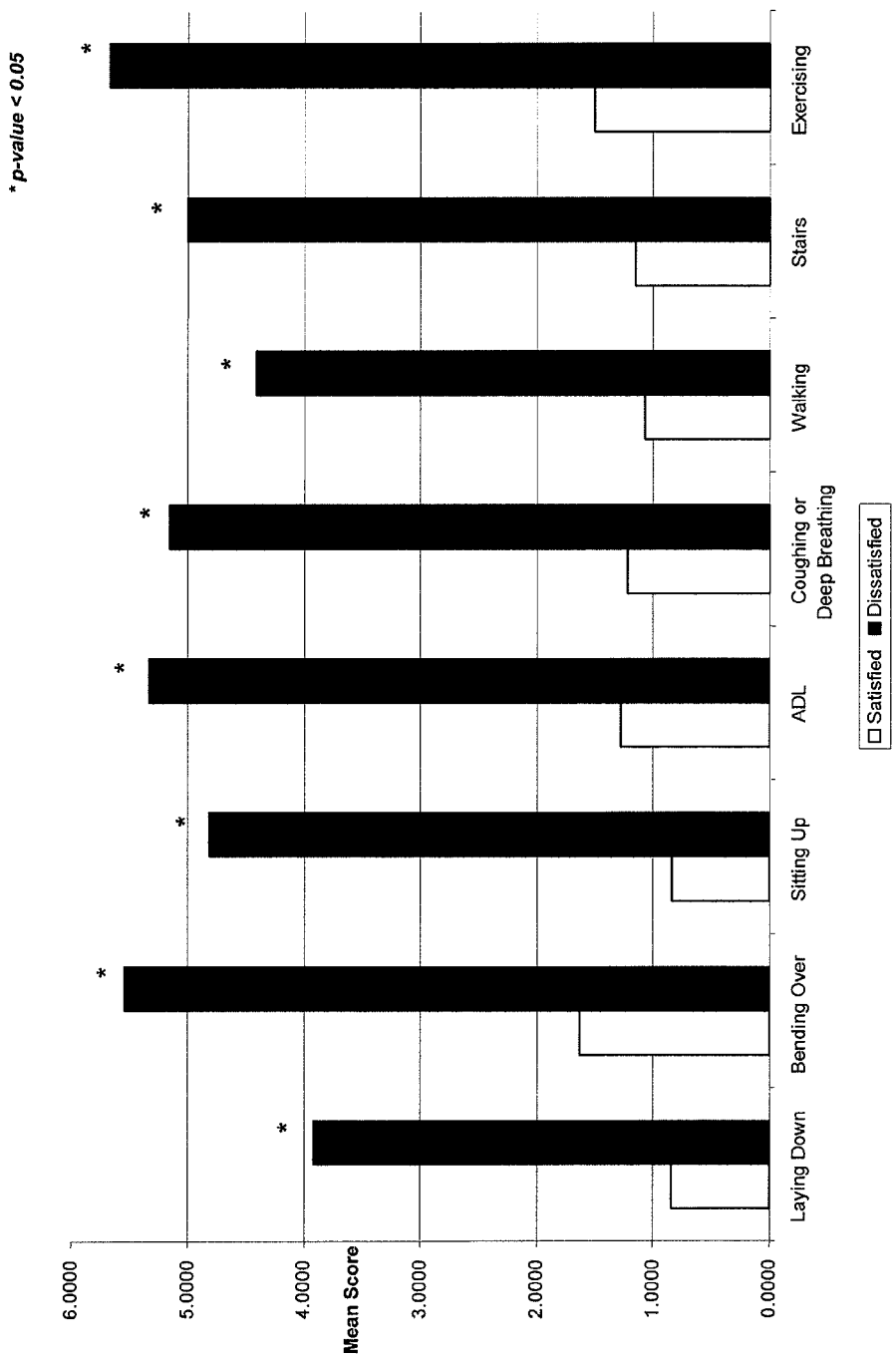
FIG. 1 is a chart demonstrating patients' overall satisfaction or dissatisfaction with the effects of various prosthetic meshes utilizing a CS questionnaire.

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide systems, computer program products, and methods for determining a hernia repair procedure for a pre-operative patient. In general, a short, disease-specific quality of life questionnaire (such as the comfort scale questionnaire described below) is administered to a number of patients who have undergone a hernia repair procedure. The responses collected from the post-operative patients are scored and associated with at least one characteristic of the procedure as well as at least one characteristic of the post-operative patient. The data is then analyzed to determine an optimum hernia repair procedure (e.g., the hernia repair procedure that may result in the least adverse effect on the patient's post-operative quality of life) for a pre-operative patient having certain characteristics based on the scores and associated characteristics of the collected responses.

The Comfort Scale (CS) Questionnaire

In embodiments of the systems, computer program products, and methods provided, a disease-specific quality of life questionnaire is administered to one or more patients who have previously undergone a hernia repair procedure in which a prosthetic mesh was used to repair the hernia. For example, a comfort scale (CS) questionnaire may be administered to post-operative patients. Each CS questionnaire may include a number of questions with each question relating to the effect of the hernia repair procedure on an aspect of the post-operative patient's quality of life, such as lying down, bending over, sitting up, walking, exercising, walking up stairs, activities of daily life, coughing, and/or deep breathing. For each such activity, symptoms experienced by the post-operative patient, such as the severity of pain, sensation of the mesh, and limitations in movement (as well as combinations thereof), may be described. A response to the CS questionnaire may thus include answers to one or more of the questions as provided by the post-operative patient. In turn, each response can then be used to calculate a score, thereby providing an indication of the relative effect of the prosthetic mesh and type of operation involved in the respective hernia repair procedure on the quality of life of the post-operative patient.

In some cases, the CS questionnaire comprises a plurality of questions relating to severity of pain, sensations of the prosthetic mesh, and limitations in movement experienced by a patient in connection with performing at least five of the following activities: lying down, bending over, sitting up, walking, exercising, walking up stairs, activities of daily life, and coughing/deep breathing. In some forms, the CS questionnaire may include 6, 7, or 8 of the activities listed above.

A rating indicative of the effect of the associated hernia repair procedure on the post-operative patient's quality of life may be used to answer each question. For example, the rating may be in the form of a numerical scale that ranges from 0 to 5, as shown in Table 1. In this case, a post-operative patient responding to the questionnaire may answer a particular question with a value of 0 to indicate that the patient does not experience any of the symptoms in question when performing the particular activity. Likewise, the post-operative patient may answer with a value of 5 to indicate that the post-operative patient experiences disabling symptoms. Answers involving a rating of 1 through 4 may thus indicate intermediate levels of the symptom in question, such as "mild but not bothersome symptoms" (corresponding to a rating of 1), "mild and bothersome, but not daily" (corresponding to a rating of 2), "moderate and/or daily symptoms" (corresponding to a rating of 3), and "severe symptoms" (corresponding to a rating of 4). For example, in answering the question of whether the post-operative patient experiences any pain when sitting up, a value of 1 would indicate that the respondent experiences mild, but not bothersome, pain when sitting up. However, various other scales (such as 0 to 10) may be used to provide further qualification of the degree of the symptoms experienced by the post-operative patient for each activity, provided that the breadth of the scale offers sufficient sensitivity. Furthermore, the ratings may be defined in various ways as long as such definitions are provided to the post-operative patient responding to the questionnaire.

If a numerical rating system is used, such as described above, the ratings provided as an answer to each question of the questionnaire may be added to provide an overall score for the response. In the previous example of a questionnaire with a rating system of 0 to 5, where 0 indicates no symptoms for the given activity and 5 indicates disabling symptoms, a lower cumulative score would correspond to a lesser adverse effect of the hernia repair procedure on the quality of life of the patient, while a higher cumulative score would indicate that the hernia repair procedure had (has) a greater adverse effect on the patient's quality of life.

Table 1 provides an example of the questions that may be included in a CS questionnaire and ratings that may be used in the response. In this example, provided for purposes of illustration only and not to be construed as limiting the invention in any way, the CS questionnaire is a 23-item questionnaire that measures the severity of pain, sensation of the mesh, and movement limitations due to the mesh in the following eight categories: lying down (LD), bending over (BO), sitting up (SU), activities of daily life (ADL), coughing or deep breathing (CB), walking (W), stairs (S), and exercise (E). The CS questionnaire score is derived by adding the ratings from each of the 23 items. In this form, the best possible score is zero and the worst possible score is 115.

TABLE 1

Representative Example of CS Questionnaire

1. While laying down, do you have

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |

2. While bending over, do you have

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |
| Movement limitations | 0 | 1 | 2 | 3 | 4 | 5 | N/A |

3. While sitting up, do you have

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |
| Movement limitations | 0 | 1 | 2 | 3 | 4 | 5 | N/A |

4. While performing activities of daily living

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |
| Movement limitations | 0 | 1 | 2 | 3 | 4 | 5 | N/A |

5. When coughing or deep breathing, do you have

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |
| Movement limitations | 0 | 1 | 2 | 3 | 4 | 5 | N/A |

6. While walking, do you have

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |
| Movement limitations | 0 | 1 | 2 | 3 | 4 | 5 | N/A |

7. While walking up the stairs, do you have

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |
| Movement limitations | 0 | 1 | 2 | 3 | 4 | 5 | N/A |

8. While exercising, do you have

| | | | | | | |
|---|---|---|---|---|---|---|
| Sensation of mesh | 0 | 1 | 2 | 3 | 4 | 5 | N/A |
| Severity of Pain | 0 | 1 | 2 | 3 | 4 | 5 | N/A |
| Movement limitations | 0 | 1 | 2 | 3 | 4 | 5 | N/A |

0 = No Symptoms
1 = Mild but not bothersome symptoms

TABLE 1-continued

Representative Example of CS Questionnaire

2 = Mild and bothersome but not daily
3 = Moderate and/or daily symptoms
4 = Severe symptoms
5 = Disabling symptoms As shown in Table 1, the illustrated questionnaire is directed to a post-operative hernia patient's sensation of prosthetic mesh, pain, and movement limitations when engaging in eight activities: lying down, bending over, sitting up, performing activities of daily living, coughing or deep breathing, walking, walking up stairs, and exercising. Patients are asked to rate the symptoms on a scale from 0 to 5 (0—No symptoms, 1—Mild but not bothersome symptoms, 2—Mild and bothersome but not daily, 3—Moderate and/or daily symptoms, 4—Severe symptoms, and 5—Disabling symptoms).

The first question in Table 1 deals with sensation of prosthetic mesh and pain while lying down and assesses the patient's discomfort or sensation of the foreign material when the patient is comfortable (e.g., not engaging in any activity). Since the patient is not moving in this question, the movement limitation question can optionally be omitted from the CS questionnaire. The second question in Table 1 deals with the patient's sensation of the prosthetic mesh, pain, and movement limitations when the patient is bending over—a common everyday activity that stretches the abdominal region. It has been generally been found that patients may experience prosthetic mesh related symptoms when bending over due to the stretching of the abdominal region.

The third question deals with the patient's sensation of the prosthetic mesh, pain, and movement limitations when sitting up. Sitting up is a common daytime activity and, although it takes less energy than many activities, patients can still have pain, sense the foreign material, or experience movement limitations in this position. The fourth question deals with the patient's sensation of the prosthetic mesh, pain, and movement limitations when the patient is engaging in activities of daily living. This question helps to evaluate the effects of the prosthetic mesh on the quality of life of the patient while performing day-to-day activities that use various muscle groups and involve different parts of the body. Such day-to-day activities may include getting out of bed, bathing, getting dressed, eating, etc.

The fifth question in Table 1 deals with the patient's sensation of the prosthetic mesh, pain, and movement limitations when coughing or deep breathing. Coughing tends to increase intra-abdominal pressure and can cause increased pain or the feeling of the foreign material. The sixth question deals with the patient's sensation of the prosthetic mesh, pain, and movement limitations when walking—another common, daily activity that causes "twisting of the abdominal wall" and requires the patient to be in the upright position.

The seventh question deals with the patient's sensation of the prosthetic mesh, pain, and movement limitations when walking up stairs. Although this question seems similar to the question dealing with walking, walking and walking up stairs involve different body motions and the use of different muscle groups. Walking up stairs is a common activity that involves bending one's legs at the waist, which could cause pain, sensation of the mesh, or movement limitations, especially for those who have undergone inguinal hernia repair. The eighth question deals with the patient's sensation of the prosthetic mesh, pain, and movement limitations when exercising—a more rigorous and physically-demanding activity.

The CS questionnaire can be used to assess both the short-term and long-term effects of a hernia repair procedure on the quality of life of a patient. For example, the CS questionnaire may be administered to a post-operative patient at various times after the surgery to evaluate the patient's progress or recovery and to identify any long-term effects of the procedure. A post-operative patient may, for example, respond to the same questionnaire 4 to 8 months after surgery, 8 to 12 months after surgery, and 18 to 24 months after surgery. In some cases, more frequent responses may be requested immediately following the surgery (e.g., three responses within the first 6 months after surgery), with fewer responses requested after 6 months has passed (e.g., one response every 6 to 12 months after the first 6 months).

As previously described, the cumulative score of the questionnaire can be used to compare the relative effect of the hernia repair procedure on the post-operative patient's quality of life in comparison to other hernia repair procedures. For example, the type of mesh used in the procedure (such as 3DMax®, DualMesh®, DualMesh® Plus, Kugel™, Marlex®, or Prolene® meshes, or heavyweight versus lightweight meshes) as well as the type of operation (such as laparoscopic versus open ventral versus open inguinal repair) may be evaluated based on the cumulative score of questionnaires administered to post-operative patients having undergone that particular type of hernia repair procedure. In some cases, the resulting scores can also be used to compile statistical data that can be used to make comparisons between various meshes and operations, as well as between different patients. Thus, the resulting scores for various prosthetic meshes and types of operations can be compiled and statistically compared using known methods of statistical analysis and as described below.

Effectiveness of CS Questionnaire

In the following example, the CS questionnaire was evaluated to determine its usefulness for measuring the effects of a prosthetic mesh on the quality of life of a patient who has undergone a hernia repair procedure. Additionally, the effectiveness of the questionnaire was compared to the Rand 36-Item Health Survey (the SF-36® questionnaire). The SF-36® questionnaire is a widely used instrument for measuring health states. The "SF" stands for "Short Form" and reflects the fact that the survey's 36-item battery is drawn from an earlier, 149 item "Long Form" version developed for the RAND Corporation® Health Insurance Experiment and Medical Outcomes Study.

The CS questionnaire was mailed to 1048 patients to assess its acceptability, responsiveness, and psychometric properties. The survey sample included patients who were at least 6 months post-operative to surgical hernia repair with mesh. The inclusion criteria for this study consisted of patients who had undergone surgical hernia repair with mesh from 2002 to 2005 at Carolinas Medical Center in Charlotte, N.C. by a group of 16 general surgeons. Patients were asked to fill in both the SF-36® questionnaire and CS questionnaire and to state their overall satisfaction with their present mesh condition. The questionnaires were mailed to each patient, and patients were provided with stamped, self-addressed envelopes for mailing the completed questionnaires to the project administrator. This type of method is well justified, as it has been previously demonstrated that mailed questionnaires are as valid as in-patient responses or replies obtained by telephone.

The SF-36® questionnaire measures the following eight domains of quality of life: physical functioning (PF), role-physical (RP), bodily pain (BP), general health (GH), vitality (VT), social functioning (SF), role-emotional (RE), and mental health (MH). Scores for these domains range from zero to 100, with 100 being the optimal level of function.

As previously described, the CS questionnaire included 23 questions that measure the severity of pain, sensation, and movement limitations due to the mesh in the following eight categories: lying down (LD), bending over (BO), sitting up (SU), activities of daily life (ADL), coughing or deep breathing (CB), walking (W), stairs (S), and exercise (E). The CS score is derived by adding the scores from each of the 23 items. The best possible score is zero, and the worst possible score is 115.

In addition, patients were asked the following four questions: (1) Which questionnaire do you like best? (2) Which questionnaire is easier to understand? (3) Which questionnaire was more reflective of the problems you have with your mesh? (4) Given the choice, which questionnaire would you rather fill out?

Statistical Analysis:

Mean values were compared using the Wilcoxon Rank-Sum test, and categorical data was analyzed using the Fisher-Exact test. Correlations were tested for significance using Spearman's non-parametric correlation coefficient test. Acceptability of the CS questionnaire was assessed by the amount of missing data. The psychometric properties of the CS questionnaire were analyzed in five ways. (1) Reliability of the scales was evaluated by Cronbach's $\alpha$, which measures the overall correlation between items within a scale. A level of 0.7 or higher is desirable. (2) Test-retest reliability was assessed by administering the CS questionnaire a second time and correlating those answers with the answers from the first administration. (3) Concurrent validity was assessed by correlating the scores for the CS questionnaire with those for the SF-36® questionnaire scales. (4) Discriminant validity explored the ability of the CS questionnaire to discriminate between groups of patients who are satisfied and those who are dissatisfied with their quality of life as it pertains to surgical mesh. (5) Principal component analysis was used to determine if any of the questions on the CS questionnaire could be deleted. SAS, Version 8 (Cary, N.C.) and a significance level of $p<0.05$ were used for all statistical analysis.

Patient Characteristics

A total of 136 questionnaires were returned and used in the study described above. The patient satisfaction rate was 85%. There was no significant difference in surgical technique (p-value=0.1835, Table 2) or hernia type (p-value=0.281, Table 3) among satisfied and dissatisfied patients. However, there was a significant difference in mesh type (p-value=0.0207, Table 4).

TABLE 2

| | Surgical Technique | | | |
|---|---|---|---|---|
| | Dissatisfied | | Satisfied | |
| Type | n | % | n | % |
| Laparoscopic | 9 | 60.00 | 64 | 79.01 |
| Open | 6 | 40.00 | 17 | 20.99 |

TABLE 3

Hernia Type

| Type | Dissatisfied n | Dissatisfied % | Satisfied n | Satisfied % |
|---|---|---|---|---|
| Ventral | 10 | 66.67 | 33 | 40.24 |
| Umbilical | 0 | 0.00 | 3 | 3.66 |
| Incisional | 1 | 6.67 | 3 | 3.66 |
| Inguinal | 4 | 26.67 | 42 | 51.22 |
| Lumbar | 0 | 0.00 | 1 | 1.22 |

TABLE 4

Mesh Type

| Type | Dissatisfied n | Dissatisfied % | Satisfied n | Satisfied % |
|---|---|---|---|---|
| 3DMax ® | 0 | 0.00 | 16 | 19.51 |
| DualMesh ® | 1 | 6.67 | 1 | 1.22 |
| DualMesh ® Plus | 9 | 60.00 | 24 | 29.27 |
| Kugel ™ | 0 | 0.00 | 1 | 1.22 |
| Marlex ® | 4 | 26.67 | 38 | 46.34 |
| Prolene ® | 1 | 6.67 | 2 | 2.44 |

Acceptability of the Questionnaire

Of the returned CS questionnaires 14.7% (n=20) had at least one missing item and 16.2% (n=22) of the SF-36® questionnaires had at least one missing item. In addition, 72% of patients preferred the CS questionnaire, 80% felt it was easier to understand, 66% felt it was more reflective of their condition, and 69% said they would rather fill it out over the SF-36® questionnaire.

Reliability

The global Cronbach's a coefficient was 0.979 and the deleted variable coefficients ranged from 0.978 to 0.979 (Table 5).

TABLE 5

Scale Reliability of the CS Questionnaire

| Domain | Cronbach's α Coefficient | Content |
|---|---|---|
| Laying Down | 0.978933 | Sensation of Mesh |
|  | 0.979546 | Pain |
| Bending Over | 0.979684 | Sensation of Mesh |
|  | 0.979046 | Pain |
|  | 0.978821 | Movement Limitations |
| Sitting | 0.979175 | Sensation of Mesh |
|  | 0.978526 | Pain |
|  | 0.978818 | Movement Limitations |
| ADL | 0.979487 | Sensation of Mesh |
|  | 0.978694 | Pain |
|  | 0.978676 | Movement Limitations |
| CB | 0.979434 | Sensation of Mesh |
|  | 0.978905 | Pain |
|  | 0.978721 | Movement Limitations |
| Walking | 0.979293 | Sensation of Mesh |
|  | 0.978778 | Pain |
|  | 0.978688 | Movement Limitations |
| Stairs | 0.979487 | Sensation of Mesh |
|  | 0.978916 | Pain |
|  | 0.979269 | Movement Limitations |
| Exercise | 0.979639 | Sensation of Mesh |
|  | 0.978654 | Pain |
|  | 0.978797 | Movement Limitations |
| Global | 0.979938 |  |

Concurrent Validity

Concurrent validity was assessed based on the correlations between the scores of the CS and SF-36® questionnaires. Except for general health, all Spearman rank correlation coefficients between the CS questionnaire total score and the SF-36® questionnaire domains were significant (p-value<0.05, Table 6). In addition, all of the CS domains were significantly correlated with all of the SF-36® questionnaire domains (p-value<0.05, Table 7), except for general health. The significant correlations ranged from 0.36 to 0.71 in absolute value, with the highest correlation being between the SF-36® questionnaire category "bodily pain" and the CS questionnaire category "stairs."

TABLE 6

Correlation of Total CS Score with SF-36 ® Domains

| Category | P-value | Correlation |
|---|---|---|
| Physical Functioning | <0.0001 | −0.4037 |
| Role Physical | <0.0001 | −0.42249 |
| Bodily Pain | <0.0001 | −0.66357 |
| General Health | 0.4027 | 0.07877 |
| Vitality | <0.0001 | −0.41948 |
| Social Function | <0.0001 | −0.42361 |
| Role Emotional | <0.0001 | −0.3698 |
| Mental Health | <0.0001 | −0.43771 |
| PCS | <0.0001 | −0.44816 |
| MCS | 0.0001 | −0.36193 |

TABLE 7

Correlation of CS Domains with SF-36 ® Domains (p-value)

| Category | Laying Down | Bending Over | Sitting | ADL | CB | Walking | Stairs | Exercise |
|---|---|---|---|---|---|---|---|---|
| Physical Functioning | −0.46 (<0.0001) | −0.61 (<0.0001) | −0.56 (<0.0001) | −0.62 (<0.0001) | −0.62 (<0.0001) | −0.66 (<0.0001) | −0.56 (<0.0001) | −0.57 (<0.0001) |
| Role Physical | −0.39 (<0.0001) | −0.54 (<0.0001) | −0.49 (<0.0001) | −0.56 (<0.0001) | −0.56 (<0.0001) | −0.57 (<0.0001) | −0.50 (<0.0001) | −0.54 (<0.0001) |
| Bodily Pain | −0.63 (<0.0001) | −0.69 (<0.0001) | −0.58 (<0.0001) | −0.61 (<0.0001) | −0.61 (<0.0001) | −0.66 (<0.0001) | −0.71 (<0.0001) | −0.59 (<0.0001) |
| General Health | −0.04 (0.6152) | −0.04 (0.6482) | 0.01 (0.8783) | 0.11 (0.2185) | −0.02 (0.7408) | 0.03 (0.6608) | 0.01 (0.8605) | 0.04 (6543) |
| Vitality | −0.44 (<0.0001) | −0.53 (<0.0001) | −0.46 (<0.0001) | −0.53 (<0.0001) | −0.53 (<0.0001) | −0.57 (<0.0001) | −0.56 (<0.0001) | −0.50 (<0.0001) |
| Social | −0.47 | −0.52 | −0.52 | −0.51 | −0.55 | −0.55 | −0.54 | −0.60 |

TABLE 7-continued

Correlation of CS Domains with SF-36 ® Domains (p-value)

| Category | Laying Down | Bending Over | Sitting | ADL | CB | Walking | Stairs | Exercise |
|---|---|---|---|---|---|---|---|---|
| Function | (<0.0001) | (<0.0001) | (<0.0001) | (<0.0001) | (<0.0001) | (<0.0001) | (<0.0001) | (<0.0001) |
| Role | −0.36 | −0.51 | −0.46 | −0.50 | −0.55 | −0.55 | −0.50 | −0.50 |
| Emotional | (<0.0001) | (<0.0001) | (<0.0001) | (<0.0001) | (<0.0001) | (<0.0001) | (<0.0001) | (<0.0001) |
| Mental | −0.41 | −0.52 | −0.52 | −0.57 | −0.61 | −0.57 | −0.52 | −0.57 |
| Health | (<0.0001) | (<0.0001) | (<0.0001) | (<0.0001) | (<0.0001) | (<0.0001) | (<0.0001) | (<0.0001) |
| PCS | −0.54 | −0.66 | −0.59 | −0.64 | −0.61 | −0.64 | −0.62 | −0.59 |
|  | (<0.0001) | (<0.0001) | (<0.0001) | (<0.0001) | (<0.0001) | (<0.0001) | (<0.0001) | (<0.0001) |
| MCS | −0.36 | −0.47 | −0.46 | −0.50 | −0.55 | −0.52 | −0.50 | −0.52 |
|  | (<0.0001) | (<0.0001) | (<0.0001) | (<0.0001) | (<0.0001) | (<0.0001) | (<0.0001) | (<0.0001) |

Discriminant Validity

Discriminant validity was assessed by comparing the CS questionnaire scores for patients who were satisfied and dissatisfied. For all CS questionnaire domains and total score, the mean scores for the satisfied patients were significantly different than those for dissatisfied patients (p-value<0.05). Moreover, when stratifying the data by mesh type, all CS questionnaire domains and total score remained significant (p-value<0.05). In comparison, the mean scores for the satisfied patients were not significantly different than those for the dissatisfied patients (p-value<0.05) in the SF-36® questionnaire domains of general health and mental health, as well as the mental condition summary score (MCS). Furthermore, after stratifying the data by mesh type, all SF-36® questionnaire domains except bodily pain were insignificantly associated with satisfaction for patients with the Marlex® mesh.

Principal Component Analysis

Principal component analysis identified 2 components with a relatively good distribution of variance, with the first component explaining approximately 70% of the variance. The loadings for the first component were extremely similar in weight.

Due to the complexities involving quality of life measures, it is very important to consider what purpose the measure is going to serve when choosing between generic and disease-specific measures. Disease-specific quality of life measures may be more sensitive for the detection and quantification of small changes that are important to clinicians or patients. In contrast, generic measures are primarily used to compare outcomes across different populations and interventions. Thus, an object of the CS questionnaire used in embodiments of the present invention was to provide a quality of life questionnaire that is sensitive enough to detect small, but significant, changes in quality of life but can also measure up to the SF-36® questionnaire, the "gold standard" of generic instruments. Satisfaction was chosen as an endpoint because the primary goal of surgical therapy is to relieve the patient's symptoms.

To further test the appropriateness of the CS questionnaire for the purpose of quantifying patient quality of life as it pertains to surgical mesh, the CS questionnaire was validated by assessing its acceptability, responsiveness, and psychometric properties. After assessing all of the psychometric properties, it was apparent that the CS questionnaire exhibits internal consistency, test-retest reliability, concurrent validity, and discriminant validity. Furthermore, this study suggests that the CS questionnaire is superior to the SF-36® questionnaire for measuring symptom severity and quality of life in patients that have undergone mesh hernia repair procedures.

As previously described, the SF-36® questionnaire measures eight domains of health-related quality of life. These include physical functioning (PF)—limitations related to health problems; role-physical (RP)—limitations in the ability of the patient to perform activities they find important because of physical limitations; bodily pain (BP)—physical pain suffered by the patient; role-emotional (RE)—the emotional effects of the patient's limitations in daily activities; general health (GH)—the patient's perceptions of his or her health; vitality (VT)—the patient's sense of vigor or malaise; social function (SF)—the ability of the patient to participate in social activities; and mental health (MH)—the patient's level of depression and anxiety. Although none of these measures explicitly address mesh symptom severity, living with the mesh can affect each of these domains.

Figure 2:
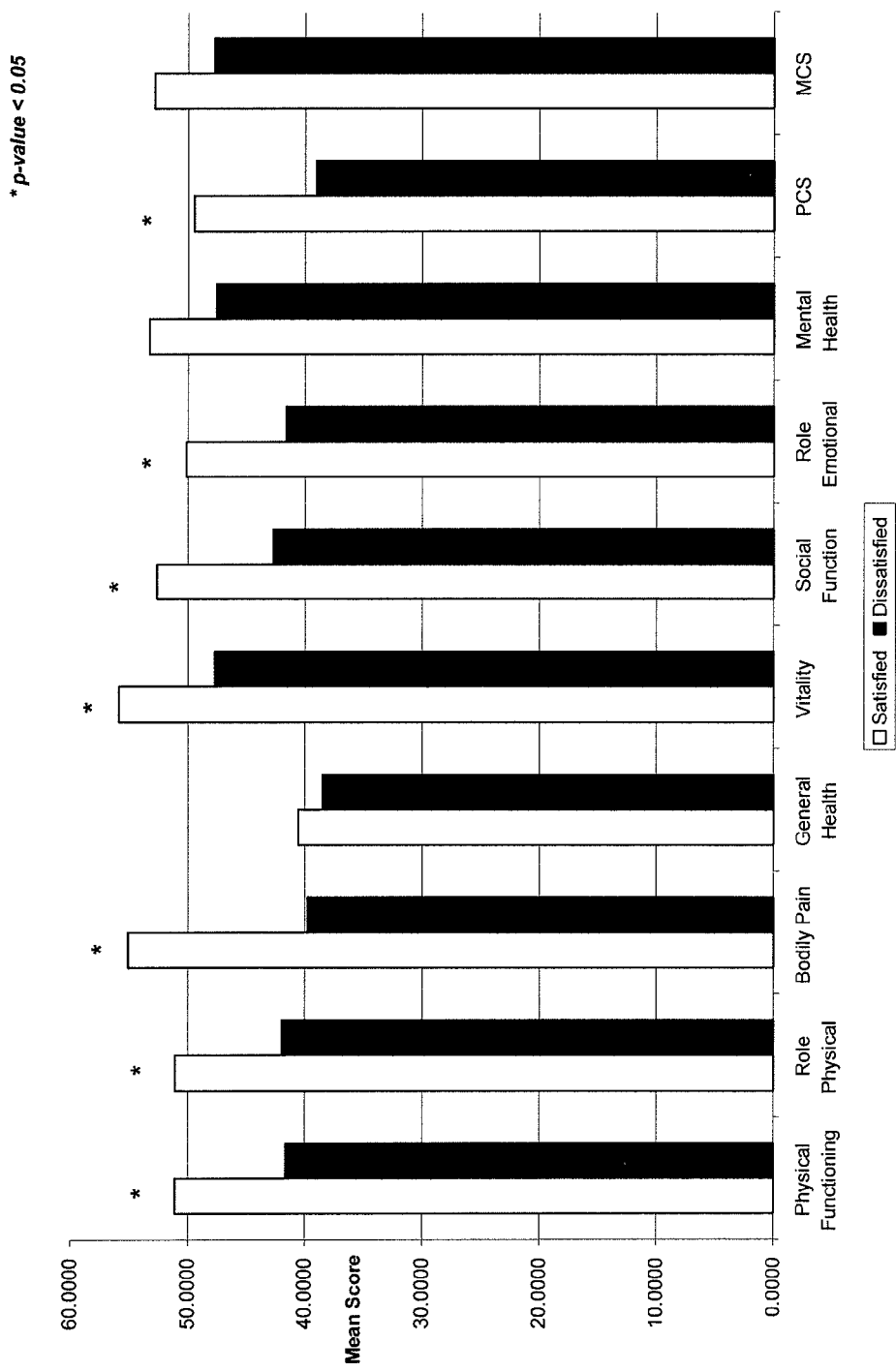
FIG. 2 is a chart demonstrating patients' overall satisfaction or dissatisfaction with the effects of various prosthetic meshes utilizing an SF-36® questionnaire.
Figure 3:
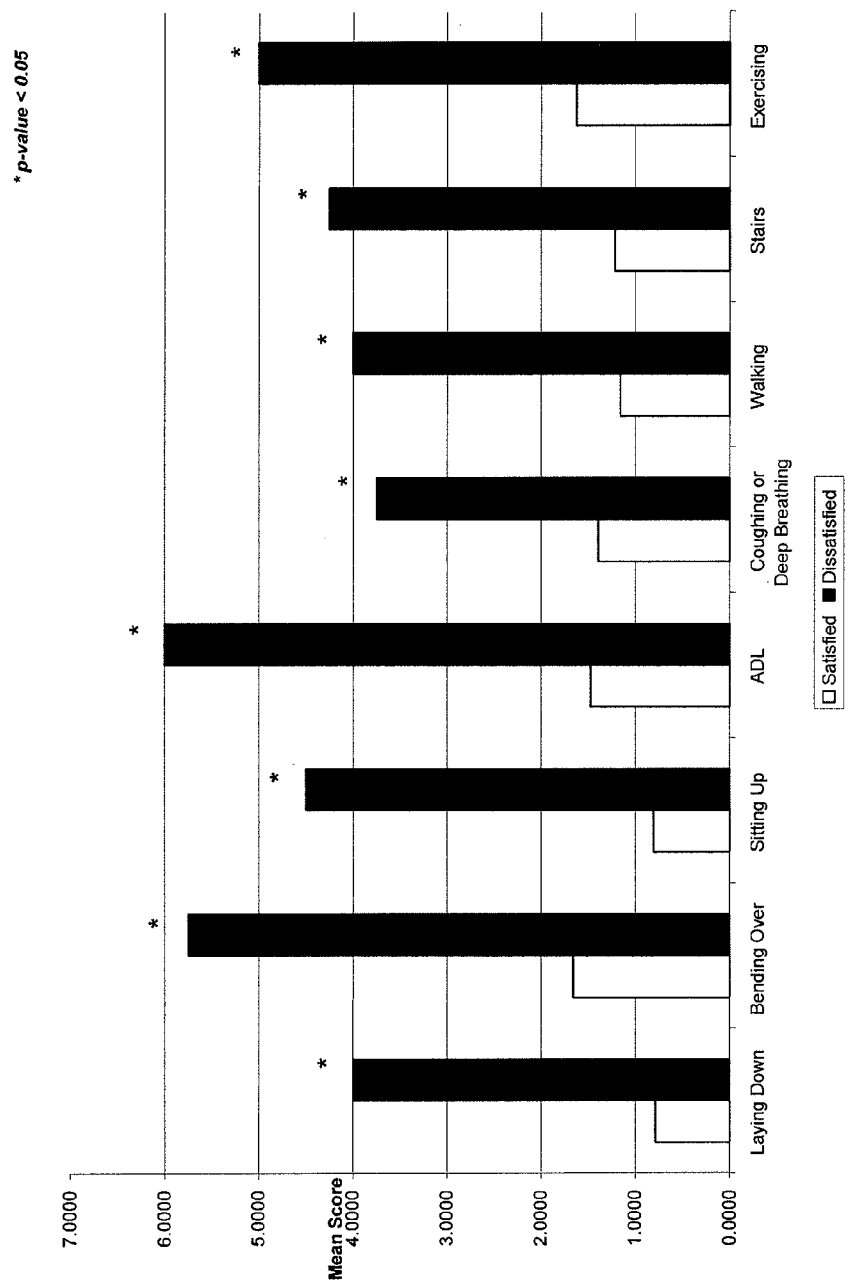
FIG. 3 is a chart demonstrating patients' overall satisfaction or dissatisfaction with the effects of a Marlex® prosthetic mesh utilizing the CS questionnaire.
Figure 4:
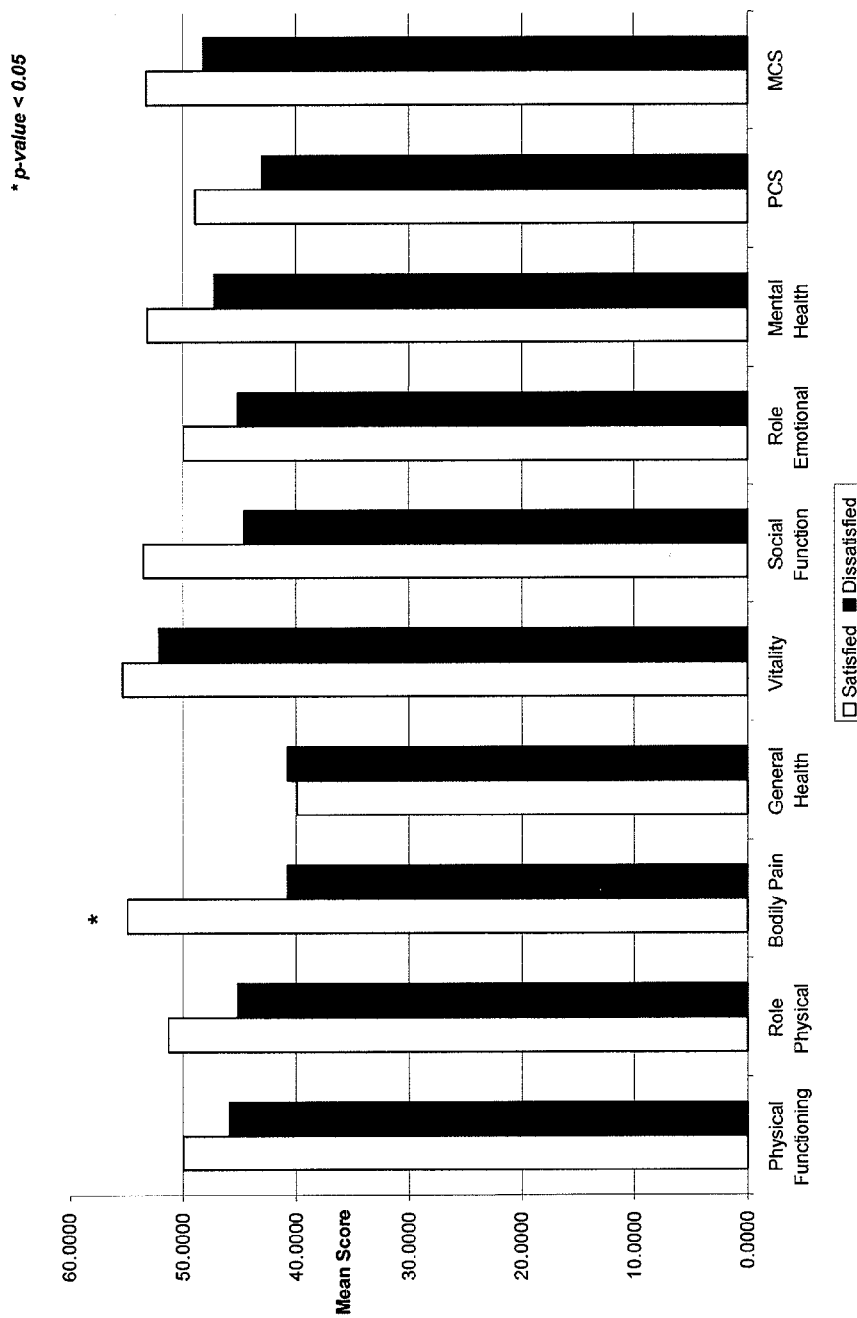
FIG. 4 is a chart demonstrating patients' overall satisfaction or dissatisfaction with the effects of a Marlex® prosthetic mesh utilizing the SF-36® questionnaire.
Figure 5:
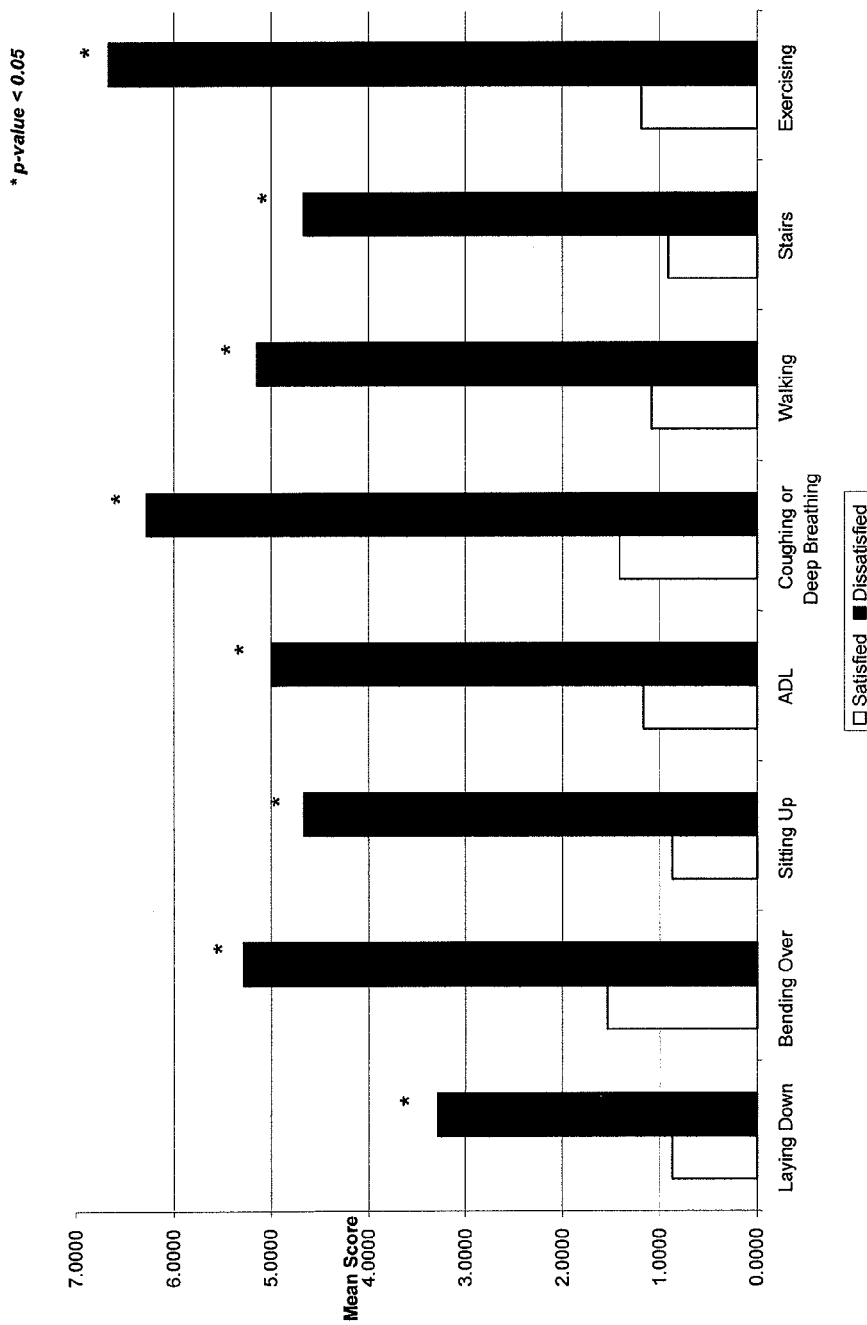
FIG. 5 is a chart demonstrating patients' overall satisfaction or dissatisfaction with the effects of a DualPlus® prosthetic mesh utilizing the CS questionnaire.
Figure 6:
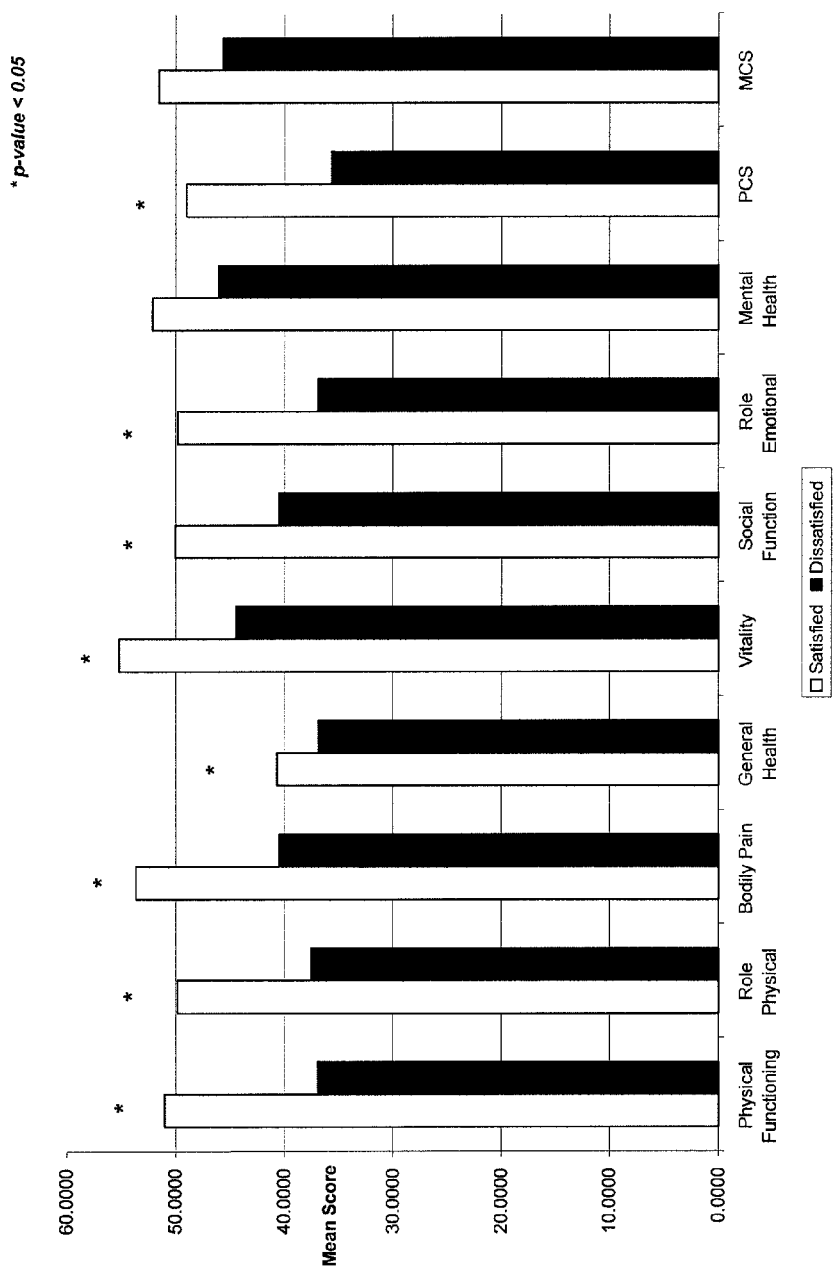
FIG. 6 is a chart demonstrating patients' overall satisfaction or dissatisfaction with the effects of a DualPlus® prosthetic mesh utilizing the SF-36® questionnaire.

FIGS. 1-6 depict the satisfaction or dissatisfaction of post-operative patients with the effects on quality of life as measured by the CS questionnaire (FIGS. 1, 3, and 5) and the SF-36® questionnaire (FIGS. 2, 4, and 6). FIGS. 1 and 2 include data for all mesh types included in Table 4 above; FIGS. 3 and 4 include data for the Marlex® mesh only; FIGS. 5 and 6 include data for the DualPlus® mesh only. Notably, FIG. 2 demonstrates that for the majority of the patients sampled, living with mesh does not seem to affect one's general health or mental health.

This raises the question of the use of generic instruments, such as the SF-36® questionnaire, for surgical therapy of hernias. In a previous study involving patients with an inguinal hernia, the SF-36® questionnaire could not measure the difference between pre-treatment and post-treatment quality of life. This demonstrates that the SF-36® questionnaire has poor discriminatory powers for satisfied and dissatisfied patients who have undergone mesh repairs. It has been shown that some conditions that are amenable to surgical therapy but only affect a limited aspect of the patient's quality of life, such as gastroesophageal reflux disease, may not be best measured by such generic scales. Based on the results of the example described above, it is apparent that hernia repair is another such condition; therefore, a mesh-specific or hernia-specific instrument is crucial for effectively understanding how surgical repair with mesh impacts patient quality of life.

Recent evidence indicates that 3% to 6% of patients will have severe pain and more than 30% will have mild pain one year after a hernia repair procedure. However, the extent to which post-operative chronic pain interferes with function has not been well described. In a study which compared laparoscopic and open repair of inguinal hernias, laparoscopic hernia repair offered an advantage to patients in terms of their early post-operative pain. Moreover, long term results show that laparoscopic repair of inguinal hernias are associated with significantly less paresthesia and groin pain than open repairs in patients at least five years after surgery. Despite such differences in specific aspects of patient health state for laparoscopic and open surgical techniques, they were not reflected in the general perceptions of health on the SF-36® questionnaire. The advantages of the laparoscopic technique were evident in the categories of movement and coughing, but not at rest—categories that the CS questionnaire specifically addresses. Therefore, it is clear that the CS questionnaire is superior to the SF-36® questionnaire in its content and focus when specifically applied to hernia repair procedures.

This example demonstrates that the CS questionnaire—a short, disease-specific quality of life questionnaire—is a better predictor of patient-perceived symptoms and satisfaction for mesh hernia repairs than the generic SF-36® questionnaire.

Factors Affecting Quality of Life Outcomes as Measured by the CS Questionnaire

Type of Operation. Laparoscopic Versus Open Ventral Hernia Repair

In the following example, quality of life outcomes in symptomatic patients undergoing laparoscopic and open ventral hernia repairs were compared using both the SF-36® questionnaire and the CS questionnaire, which are described above. The hernias were classified as symptomatic if the patient reported moderate to severe pain pre-operatively on the SF-36® questionnaire. The laparoscopic and open method of surgery was discussed in detail with each patient during the informed consent procedure. Each patient was offered either a laparoscopic or open hernia repair. Ultimately, the technique of surgery was based on physician input taking into account the feasibility of the procedure and risk and benefits based on the particular patient characteristics.

For the laparoscopic hernia repairs, a standard technique was used. The patient was positioned supine with arms tucked at the sides. An orogastric tube, Foley catheter, and adhesive, antibacterial drape were placed. An open abdominal access technique was most often used to create pneumoperitoneum. A 10-mm balloon-tipped trocar was inserted through the first incision, typically just inferior to the tip of the eleventh rib on the left. When the abdomen was entered safely, two or three additional 5-mm trocars were placed laterally on the same side as the first trocar with a 5-mm trocar was placed on the opposite side of the abdomen. The adhesions to the anterior abdominal wall surrounding the hernia were lysed, and the hernia contents were reduced, and the peritoneal sac was left in situ.

After completion of the dissection, the hernia defect was measured and marked. Measurements were used to choose an appropriately sized prosthetic mesh to overlap all margins of the defect by at least 4 cm. In all cases, expanded polytetrafluoroethylene (ePTFE) mesh was used (Gore-Tex® DualMesh®, W.L. Gore & Associates, Flagstaff, Ariz.). Non-absorbable, monofilament sutures were placed at the halfway points on each side of the mesh, tied, and brought up trans-fascially. The perimeter of the mesh was then secured with 5-mm spiral tacks no more than 1-cm apart. Additional full thickness sutures were placed in the mesh every 4 cm to 6 cm circumferentially with the suture passer. Skin closure was performed with a subcuticular stitch.

For the open repair, a standardized technique was used involving a midline incision with excision of old scars. The dissection was then carried out through the subcutaneous fat, and the peritoneal cavity was entered. Adhesiolysis was performed with caution to avoid bowel injury. When adhesiolysis was completed, a preperitoneal plane was entered, and peritoneal flaps were developed circumferentially. The preperitoneal space was typically developed to the pubis and bilateral Cooper's ligaments inferiorly, the lateral edge of psoas muscles laterally, and to the level of the diaphragm and xiphoid process superiorly. When this dissection was complete, the peritoneum was re-approximated with a running absorbable suture to completely cover exposed abdominal viscera. Polypropylene mesh was placed between the peritoneum and fascia, extending circumferentially to allow for at least a 7 cm of mesh-to-defect overlap, whenever possible. To secure the mesh in place, it was first anchored with interrupted non-absorbable sutures at the pubis and Cooper's ligaments. Full thickness, transabdominal, permanent sutures incorporating the mesh were then placed inferior-laterally, laterally, and along the costal margin every 4 to 6 cm. Superiorly, the mesh was fixed in place with a transabdominal suture on each side of the xiphoid process. The sutures were passed through the abdominal wall using a curved (Reverdin) needle, and the knots were tied down in the subcutaneous tissue. In the rare instance that the preperitoneal plane could not be dissected free, the mesh was placed in the retrorectus space anterior to the posterior rectus fascia. Closed suction drains were always placed above the prosthetic and kept in place until a daily output was approximately 30 cc or less, but no longer than 5-7 days. The midline fascia was closed when possible.

Pre-operative and post-operative comparisons in quality of life scores were determined using Wilcoxon tests, with the significance level p<0.05. The study included 56 symptomatic patients who underwent ventral/incisional hernia repair. Forty-one (73%) patients chose a laparoscopic repair and fifteen (27%) patients chose an open repair. There was no statistical difference in the pre-operative scores of the SF-36® questionnaire between patients undergoing laparoscopic or open repairs (Table 8).

TABLE 8

Pre-operative SF-36 ® Scores for Symptomatic Patients with Ventral or Incisional Hernias

| Category | Laparoscopic | Open | p-value |
| --- | --- | --- | --- |
| General Health | 47.98 | 44.80 | 0.1816 |
| Vitality | 43.11 | 38.71 | 0.1968 |
| Social Function | 40.87 | 38.93 | 0.6187 |
| Role Emotional | 37.53 | 34.78 | 0.4054 |
| Mental Health | 46.28 | 40.76 | 0.1118 |
| Physical Function | 37.22 | 36.15 | 0.7066 |
| Role Physical | 35.65 | 33.59 | 0.3218 |
| Bodily Pain | 36.61 | 33.08 | 0.1493 |
| PCS[a] | 37.78 | 36.41 | 0.3170 |
| MCS[b] | 44.86 | 40.20 | 0.1902 |

[a]PCS = Physical Component Score
[b]MCS = Mental Component Score

Post-operative scores on the SF-36® questionnaire were significantly improved in the laparoscopic group compared with the open group in general health (46% vs. 37%, p=0.217), vitality (53% vs. 45%, p=0.0491), role emotional (45% vs. 35%, p=0.0480), and mental health (49% vs. 39%, p=0.0381). Physical function closely approached statistical significance with a p-value at 0.05 (Table 9).

TABLE 9

Post-operative SF-36 ® Questionnaire Scores for Symptomatic Patients with Ventral or Incisional Hernias

| Category | Laparoscopic | Open | p-value |
| --- | --- | --- | --- |
| General Health | 46.31 | 36.70 | 0.0217 |
| Vitality | 52.85 | 44.50 | 0.0491 |
| Social Function | 45.81 | 42.44 | 0.5178 |
| Role Emotional | 45.33 | 34.65 | 0.0480 |
| Mental Health | 49.18 | 39.15 | 0.0381 |
| Physical Function | 46.25 | 37.78 | 0.0504 |
| Role Physical | 45.55 | 39.59 | 0.2077 |
| Bodily Pain | 49.49 | 42.58 | 0.1390 |
| PCS[a] | 46.67 | 40.03 | 0.1175 |
| MCS[b] | 48.08 | 40.69 | 0.2075 |

[a]PCS = Physical Component Score
[b]MCS = Mental Component Score

Post-operative quality of life scores on the CS questionnaire (Table 10) were significantly improved in the laparoscopic group compared with the open group in bending over (3.15 vs. 5.87, p=0.0158), sitting up (2.51 vs. 5.13, p=0.0211), activities of daily living (2.48 vs. 5.75, p=0.0139), coughing or deep breathing (2.95 vs. 5.75, p=0.0314), walking (2.36 vs. 4.62, p=0.0427), exercising (3.19 vs. 6.14, p=0.0222), and total comfort scale (17.62 vs. 40.23, p=0.0084).

TABLE 10

Post-operative CS Questionnaire Scores for Symptomatic Patients with Ventral or Incisional Hernias

| Category | Laparoscopic | Open | p-value |
| --- | --- | --- | --- |
| Lying Down | 1.93 | 2.50 | 0.2941 |
| Bending Over | 3.15 | 5.87 | 0.0158 |
| Sitting Up | 2.51 | 5.13 | 0.0211 |
| ADL[a] | 2.48 | 5.75 | 0.0139 |
| Coughing or Deep Breathing | 2.95 | 5.75 | 0.0314 |
| Walking | 2.36 | 4.62 | 0.0427 |
| Stairs | 2.77 | 4.31 | 0.1505 |
| Exercising | 3.19 | 6.14 | 0.0222 |
| Total Comfort Scale | 17.62 | 40.23 | 0.0084 |

[a]ADL = Activities of Daily Living

The findings of improved quality of life in patients undergoing laparoscopic compared with open repairs are similar to reports for inguinal hernias. Heikkinen and colleagues compared long term outcomes and chronic pain following laparoscopic transabdominal preperitoneal inguinal hernia repair (TAPP) and open Lichtenstein repairs finding significantly more discomfort associated with the open Lichtenstein repairs. Other studies have reported decreased chronic pain associated with laparoscopic inguinal hernia over open repairs; however, these were comparisons with non-mesh open repairs. The majority of studies have shown improved quality of life and pain following laparoscopic inguinal hernia repair, but some have debated this. Velanovich and colleagues compared quality of life following four types of open and laparoscopic surgical procedures, cholecystectomy, esophageal surgery, inguinal hernia, and splenectomy and reported significantly improved quality of life following laparoscopic repair for all surgeries except inguinal hernia.

Several other studies have compared laparoscopic to open ventral hernia repair, reporting fewer wound related and overall complications, fewer hernia recurrences, and shorter hospital stays. These studies evaluated traditional outcomes but did not examine quality of life following open and laparoscopic procedures.

One important point and potential shortcoming of this study is that only quality of life outcomes were measured. It can be argued that evaluating this without additional outcomes, (recurrence or mesh infection) is not appropriate. However, patients having operative or perioperative complications would be expected to report decreased quality of life compared with patients without complications. It is believed that the outcomes of this study are accurate and applicable to patients with ventral hernias because the patients had similar pre-operative quality of life scores. Also, evaluating patients at least 6 months after surgery should decrease the impact that early complications have on quality of life.

Another interesting issue relates to the results obtained from the two different quality of life surveys. Quality of life was significantly improved in laparoscopic compared with open repairs in four of ten components on the SF-36® questionnaire and six of eight components on the CS questionnaire. The CS questionnaire was more sensitive to change since disease specific surveys are more likely than generic surveys to detect change caused by treatment. Patients prefer the CS questionnaire by a 3-to-1 ratio over the SF-36® questionnaire due to its specificity and ease of use. When examining the results from the CS questionnaire, the only non-activity parameter not significantly different between laparoscopic and open surgical methods was lying down. Curiously, there was no difference in the stairs parameter when all the other activity measures were significantly different. In the SF-36® survey, there were significant improvements after laparoscopic repair in both the physical and mental components, which infers some psychological benefit from the laparoscopic method.

Type of Prosthetic Mesh: Lightweight Versus Heavyweight

In the following example, quality of life was assessed in post-operative patients who had open inguinal hernia repairs at a single institution from January 2002 through April 2007 to evaluate the effect of the type of prosthetic mesh used in the procedure. A standard tension-free technique using heavyweight or lightweight mesh was used for repair. For example, polypropylene mesh is classified as lightweight or heavyweight based on the density of the mesh. Heavyweight mesh typically has a density of about 90-110 $g/m^2$, whereas lightweight mesh has a density less than 40 $g/m^2$, typically in the range of about 25-35 $g/m^2$, such as a density of around 30 $g/m^2$. Quality of life was assessed using the CS questionnaire described above. Higher scores on the CS questionnaire indicated a lower quality of life (more negative effects) whereas lower scores indicated a higher quality of life (fewer negative effects). Scores were compared using the Wilcoxson rank sum test, and results were considered significant if p<0.05.

Seventy-eight open inguinal hernia repairs were performed during the study period. Heavyweight mesh was used in 44 patients (56.4%), and lightweight mesh was used in 34 patients (43.6%). The mean total score on the CS questionnaire was lower for patients receiving the lightweight mesh than for patients receiving the heavyweight mesh (24.07 vs. 36.88, p=0.0028). Lower mean scores for all activities were reported by patients receiving the lightweight mesh. In particular, statistically significant results included lower mean scores for walking (33.50 vs. 35.89, p=0.013) and exercising (26.29 vs. 36.87, p=0.013). Patients receiving the heavyweight mesh had higher mean scores for mesh sensation as compared to patients receiving the lightweight mesh (37.03 vs. 24.79, p=0.003) and experienced more movement limitations than their lightweight counterparts (34.61 vs. 26.75, p=0.033).

Based on these results, quality of life following open inguinal hernia repair is significantly affected by the choice of prosthetic mesh. Patients complained of increased sensation of the mesh, movement limitations, and lower overall quality of life following hernia repair with heavyweight mesh. The user of lightweight mesh improves quality of life compared to heavyweight mesh following open inguinal hernia repair.

Gender: Male Versus Female Patients

In the following example, quality of life was assessed in post-operative patients who had open ventral hernia repairs involving heavyweight mesh to evaluate how gender affects post-operative quality of life. Quality of life for male and female patients was assessed six months after surgery and was compared using the CS questionnaire, described above. Comparison of post-operative data between genders was performed using the Wilcoxson rank sum test, and results were considered significant if $p<0.05$.

Thirty-nine patients—15 males and 24 females—underwent open ventral hernia repair with heavyweight mesh from January 2002 through February 2007 and returned a response to a CS questionnaire six months after the procedure. The mean age of the male patients was 58.1 years, and the mean age of the female patients was 51.5 years.

The mean pain score for women was significantly higher than that for men (17.15 vs. 9.40, $p=0.012$). Also females reported more movement limitations than males (17.06 vs. 9.54, $p=0.015$). Furthermore, females were significantly more affected by mesh placement than males when lying down ($p=0.030$), bending over ($p=0.021$), performing vigorous activity ($p=0.022$), walking ($p=0.015$), and climbing stairs ($p=0.025$). The responses from female patients corresponded to a higher total score on the CS questionnaire than the responses from male patients, indicating that females experienced a lower overall quality of life following the procedure than their male counterparts (15.66 vs. 9.00, $p=0.026$).

This demonstrates that gender differences exist in quality of life following open ventral hernia repair with heavyweight mesh. Women appear more dissatisfied than men with their quality of life, experiencing more pain and movement limitations post-operatively. This suggests that the use of heavyweight mesh in women undergoing open ventral hernia repair should be reconsidered and that perhaps lightweight mesh would be a better alternative in women requiring open ventral hernia repair.

Determining an Appropriate Hernia Repair Procedure Using the CS Questionnaire

Embodiments of the present invention make use of disease-specific quality of life questionnaire, such as the CS questionnaire discussed above, in determining a hernia repair procedure for a pre-operative patient that should result in less of a negative impact on the patient's quality of life than other available hernia repair procedures. In this regard, the term "hernia repair procedure" includes various aspects of the medical procedure for repairing a hernia that are available alternatives to the patient based on the patient's diagnosis, condition, and other factors. In other words, although a doctor may prescribe one aspect of the hernia repair procedure based on an examination of the patient (such as ventral vs. inguinal repair), embodiments described below may recommend additional, alternative aspects of the procedure (such as type of mesh, e.g., lightweight or heavyweight, and surgical technique, e.g., laparoscopic vs. open, etc.).

Figure 7:
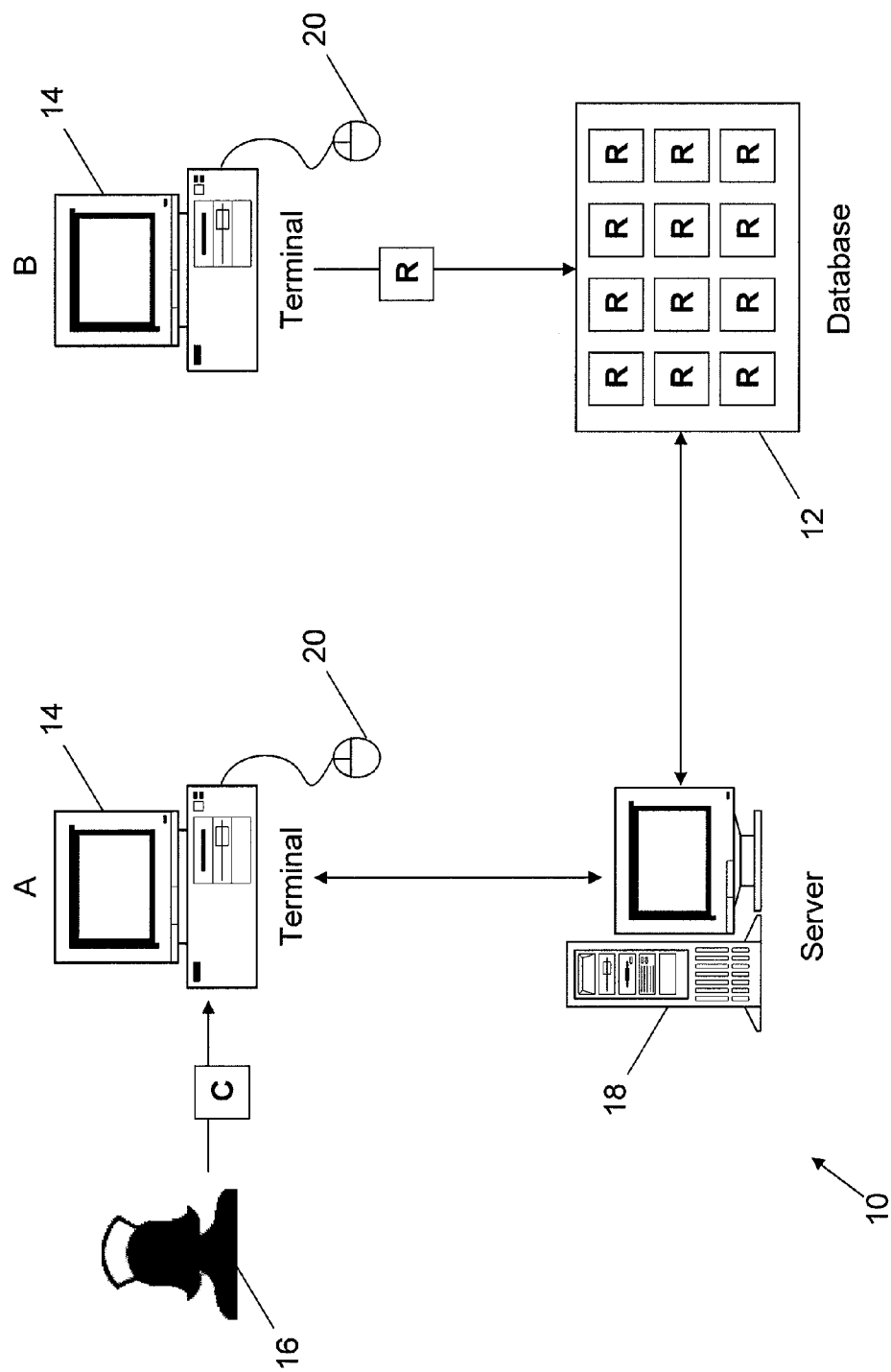
FIG. 7 illustrates a system according to an exemplary embodiment of the present invention.

A system 10 for determining a hernia repair procedure for a pre-operative patient according to one embodiment is depicted in FIG. 7. The system 10 includes a database 12 of responses R to a health questionnaire administered to a number of patients who have previously undergone a hernia repair procedure in which a prosthetic mesh was used to repair the hernia. For example, the responses R may be responses to the CS questionnaire described above. The system also includes a terminal 14 (Terminal A) configured to receive search criteria C, for example from a nurse or medical technician 16, and a server 18 in communication with the database 12 and the terminal 14.

Each response R is associated with an overall score indicative of the effect of the hernia repair procedure on an aspect of the post-operative patient's quality of life. Thus, the overall score provides a measure of the severity of pain experience by the patient, the patient's sensation of the prosthetic mesh, and limitations in movement experienced in connection with performing at least five activities. Such activities may include lying down, bending over, sitting up, walking, exercising, walking up stairs, performing activities of daily life, coughing, and deep breathing. Furthermore, each overall score is associated with at least one characteristic of the respective post-operative patient and with at least one characteristic of the respective hernia repair procedure performed.

Patient characteristics may include a number of characteristics that describe the patient status, such as the patient's age and/or gender, the type of hernia experienced, and the patient's pre-operative health, among many other factors. Procedure characteristics, likewise, may include various aspects of the hernia repair procedure performed, such as the type of operation (laparoscopic, open ventral, etc.) and the type of prosthetic mesh used (mesh material—e.g., polypropylene, polytetrafluoroethylene, etc.; brand of mesh—e.g., DualMesh® mesh, Marlex® mesh, Prolene® mesh; density of mesh—e.g., heavyweight mesh, lightweight mesh, etc.). By associating each overall score with at least one patient characteristic and at least one procedure characteristic, the overall score may have context and allow for a more meaningful analysis.

Figure 8:
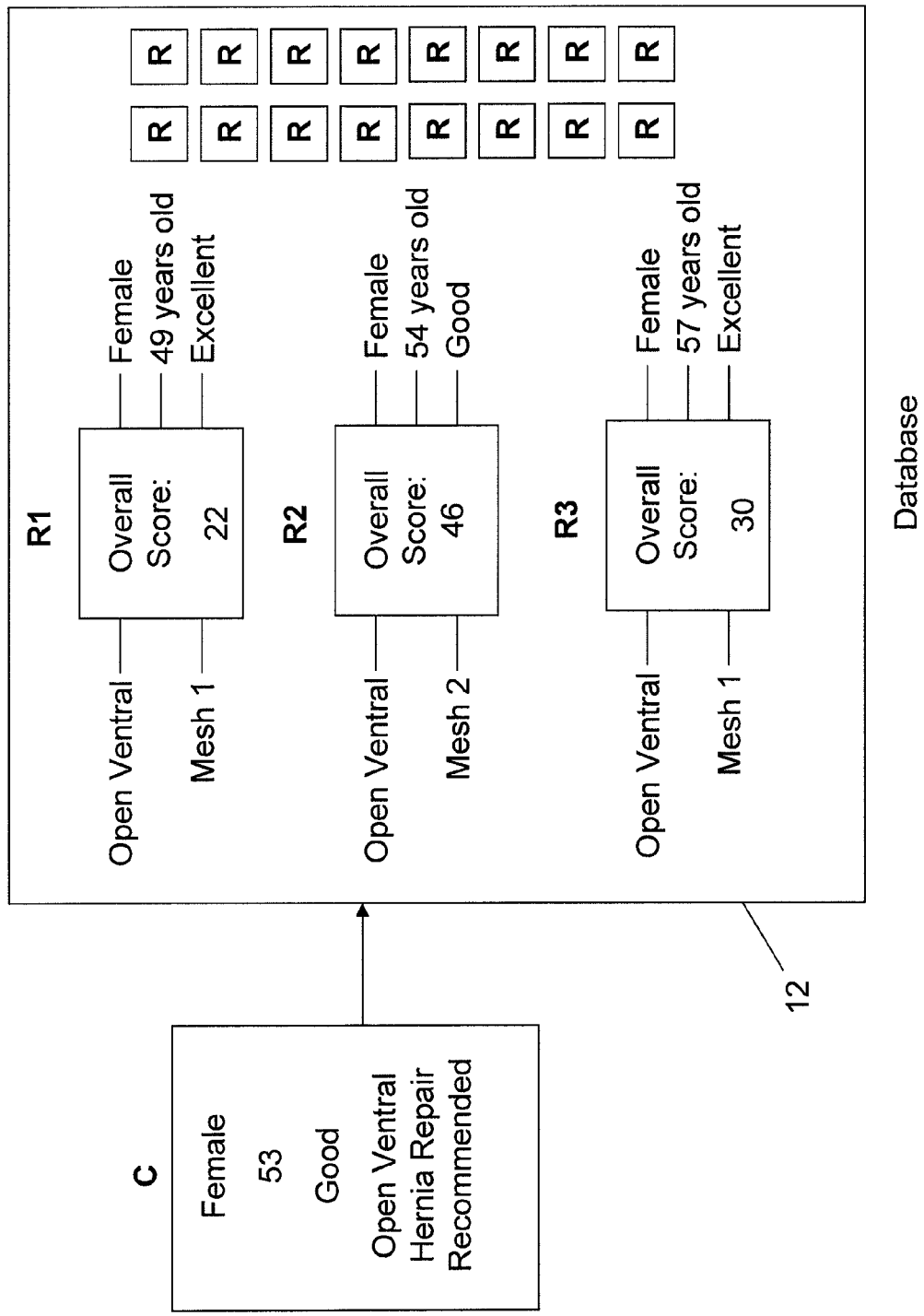
FIG. 8 illustrates an analysis of responses stored in a database according to an exemplary embodiment of the present invention.

Referring to FIG. 8, for example, one of the responses R1 stored in the database may have an overall score of 22 based on a health questionnaire in which a score of 0 indicates no negative impact on quality of life and a score of 115 indicates the worst possible impact on quality of life. Thus, an overall score of 22 in this case may indicate a mild to moderate negative impact on quality of life. The overall score of 22 may be associated with patient characteristics for a 49-year-old female having excellent pre-operative health. The corresponding procedure characteristics may reflect the fact that an open ventral hernia repair was performed using Mesh 1 (i.e., Mesh Type 1). Another response R2 may have an overall score of 46, indicating a greater negative impact on quality of life according to the same health questionnaire. The overall score of 46 may be associated with patient characteristics for a 54-year-old female having good pre-operative health. The corresponding procedure characteristics may reflect the fact that an open ventral hernia repair was performed using Mesh 2. The database 12 may include a number of other responses R, each having an overall score and associated with a patient characteristic and a procedure characteristic.

Turning again to FIG. 7, a nurse, medical technician, or other user 16 may access the terminal 14 and input search criteria C including at least one characteristic relating to a pre-operative patient. The search criteria C may include the pre-operative patient's age, gender, type of hernia, pre-operative health, and/or type of operation recommended, among many other characteristics. The user 16 may input the search criteria C via any type of input device compatible with the terminal, such as a mouse 20, keypad, touch screen, etc.

Upon receiving the search criteria C, the terminal 14 may communicate the search criteria C to the server 18. The server

18 may, in turn, be configured to query the database 12 and to determine an optimum hernia repair procedure for the pre-operative patient based on the overall scores, the associated patient characteristics, and the criteria C received. For example, the criteria C may reflect the fact that the pre-operative patient is a 53-year-old female in good pre-operative health for which an open ventral hernia repair operation has been recommended, as illustrated in FIG. 8. The server in this case may be configured to query the database 12 and to determine the optimum hernia repair procedure for the pre-operative patient to whom the criteria relates based on the responses R stored in the database.

Referring to FIGS. 7 and 8, the server 18 may be configured to analyze the responses R in the database 12 having at least one associated patient characteristic that matches at least one characteristic included in the search criteria C and to select the hernia repair procedure associated with the most matching responses having an overall score indicating the least effect of the hernia repair procedure on the respective post-operative patient's quality of life. For example, in FIG. 8, a third response R3 may have an overall score of 30 and may be associated with patient characteristics including "Female," "57 years old," and "Excellent" pre-operative health and with procedure characteristics including "Open Ventral" and "Mesh 1." From among all of the responses stored in the database 12, the server in this example would select the three responses R1, R2, R3 matching two or more of the characteristics in the criteria—in this case "Female," and "Open Ventral." Alternatively, the server may be configured to select the responses match one or more particular criteria, such as age or recommended type of hernia operation, or the server may be configured to weigh certain criteria more than other criteria when selecting matching responses.

Returning to the example, the server may then select the hernia repair procedure (i.e., type of mesh and/or type of operation) based on the greatest number of matching responses having the lowest overall score (indicating the least negative impact on quality of life). In this case, the server would select Mesh 1 to be used in the recommended open ventral hernia repair because two of the matching responses with the lowest overall scores are associated with Mesh 1. Of course, this example is greatly simplified for purposes of explanation and the server may be configured to analyze hundreds or thousands of matching responses to select the appropriate mesh, providing a more statistically justifiable result.

The server may be configured to analyze the responses R stored in the database in other ways. For example, the server may be configured to identify at least one of the responses R that has the greatest number of associated characteristics that match the search criteria and to select the hernia repair procedure associated with the identified responses having an overall score indicating the least effect of the hernia repair procedure on the respective post-operative patient's quality of life. In FIG. 8, the server may identify the second response R2 as having the greatest number of associated characteristics (3—"Female," "Good," and "Open Ventral") and thus may select Mesh 2 to be used in the recommended open ventral hernia repair. Numerous other statistical and analytical methods for determining an optimum hernia repair procedure may be used. For example, only responses having an overall score within a certain range, such as 0 to 30 for the above example, may be considered. Statistical indicators, such as Q values (the minimum false discovery rate at which the results may be called significant) and p-values (the probability of obtaining a result at least as extreme as a given data point) may also be used to give relevance to the data and potentially eliminate errant or statistically insignificant results.

Referring again to FIG. 7, the database 12, the terminal A, and the server 18 may be co-located, such as part of a single computer, or may be distributed over a network. Thus, for example, there may be multiple terminals A provided within a single medical facility or a number of medical facilities through which a user may be able to enter search criteria for determining a hernia repair procedure. The database 12, which may also be in a single location or distributed over several pieces of hardware connected to the network, may in turn be accessible by any one of the terminals A that are connected to the same network via the server 18, which may be able to determine the optimum hernia repair procedure for a requesting terminal A located in a different geographic area (e.g., a different medical facility). In this way, several medical facilities may be able to pool responses into a database 12 to achieve a more accurate statistical result for a given set of search criteria. Likewise, users responding to a questionnaire via terminals B may be at various geographic locations but may be able to store responses to a database 12 connected to the same network.

Figure 9:
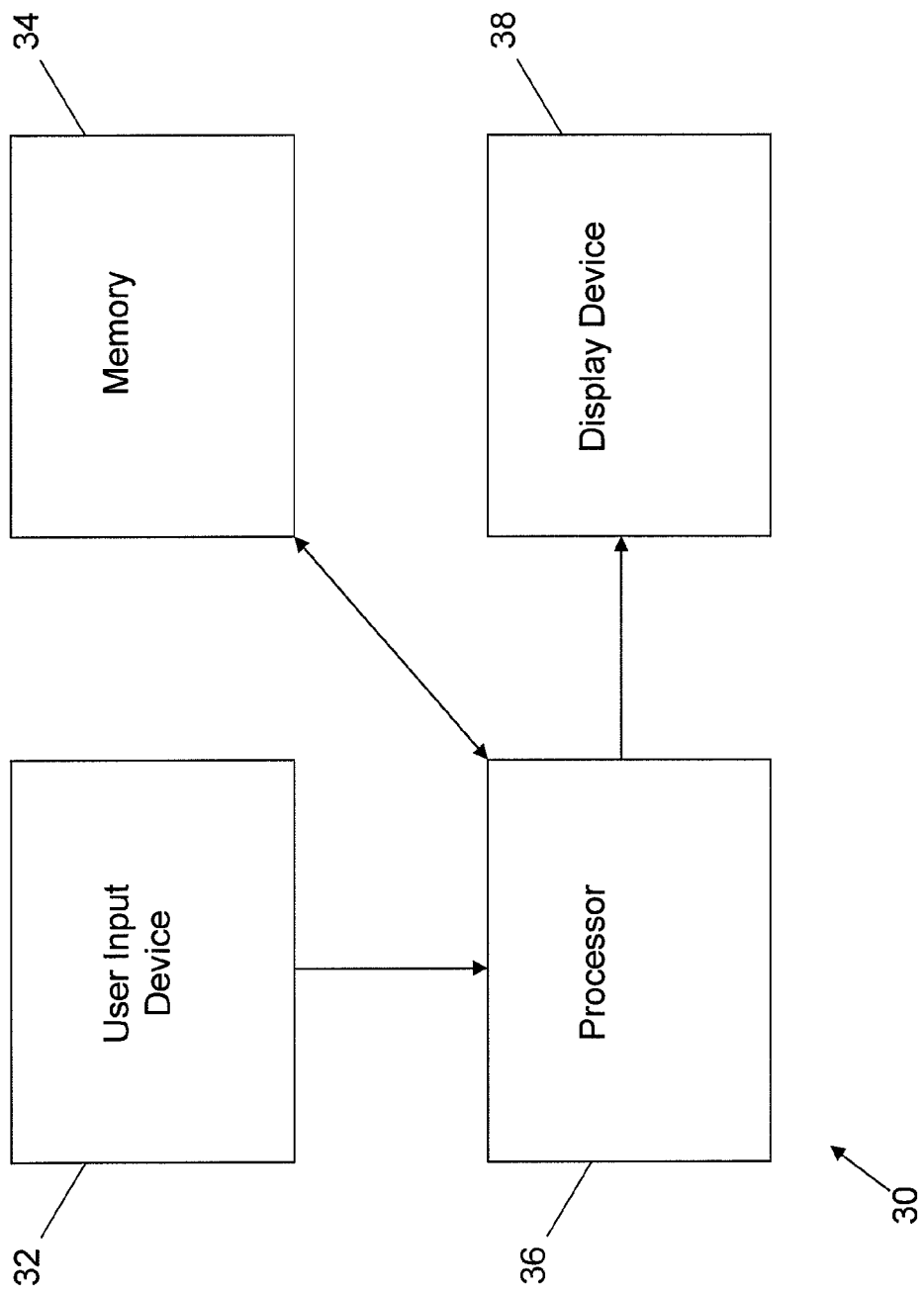
FIG. 9 is a schematic block diagram of a system according to an exemplary embodiment of the present invention.

In other embodiments, a system 30 for determining a hernia repair procedure for a pre-operative patient may include a user input device 32, a memory 34, and a processor 36, as shown in FIG. 9. The user input device 32, which may be a mouse 20 as shown in FIG. 7, a keyboard, or any other type of device that can receive input from a user, is configured to receive a response to a health questionnaire (such as the CS questionnaire) administered to a patient who has previously undergone a hernia repair procedure in which a prosthetic mesh was used to repair the hernia. As previously described, the health questionnaire may include a number of questions, and each question may relate to the effect of the hernia repair procedure on an aspect of the post-operative patient's quality of life, including severity of pain, sensations of the prosthetic mesh, and limitations in movement experienced by the post-operative patient in connection with performing at least five activities. Such activities may include lying down, bending over, sitting up, walking, exercising, walking up stairs, performing activities of daily life, coughing, and deep breathing, among others.

The memory 34 may be configured to store data, such as the input received via the user input device 32, as well as other data involved in the analysis of the input, as described below. The memory 34 may include volatile memory, such as volatile Random Access Memory (RAM) including a cache area for the temporary storage of data, and may also include other non-volatile memory, which can be embedded and/or may be removable. The non-volatile memory can additionally or alternatively comprise an EEPROM, flash memory or the like. Furthermore, the memory 34 may be structured in various ways, such as distributed through the system or disposed in a single location. The memory 34 may in some cases be a database, such as the database 12 shown in FIG. 7.

Referring again to FIG. 9, the processor 36, which is in communication with the user input device 32 and the memory 34, is configured to execute various program modules for determining the hernia repair procedure based in part on data received by the user input device 32 and stored in the memory 34. The processor 36 may be configured to execute a first program module operable for scoring the response received to determine an overall score indicative of the respective post-operative patient's quality of life.

A second program module may be operable for associating the overall score with at least one characteristic of the respective post-operative patient and with at least one characteristic of the respective hernia repair procedure performed. The patient and procedure characteristics may be included as part of the response received by the user input device 32, for example, as answers to one or more of the questions included in the health questionnaire, or may be supplied separately via the user input device 32, such as by a doctor, nurse, or other medical profession upon reviewing the stored response. For example, in some cases, the user input device 32 may be configured to receive at least one patient characteristic relating to the post-operative patient, such as the patient's age, gender, type of hernia, and pre-operative health, and may also be configured to receive at least one procedure characteristic relating to the post-operative patient, such as the type of operation performed and the type of prosthetic mesh used in the procedure. Alternatively, the patient and procedure characteristics may be accessed by the processor 36 from the memory 34 or from a separate location, such as a patient or records database, for association with the overall score.

The processor 36 may also be configured to execute a third program module operable for determining an optimum hernia repair procedure for the pre-operative patient based on the overall score and the associated patient characteristics. The processor 36 may implement any number of algorithms and/or statistical techniques to determine the hernia repair procedure that is likely to result in the least negative impact on the pre-operative patient's quality of life based on the experiences of one or more post-operative patients. The user input device 32 may be configured to receive one or more characteristics relating to the pre-operative patient, such as the pre-operative patient's age, gender, type of hernia, pre-operative health, and/or type of operation recommended, which may inform the analysis conducted by the processor 36.

In some cases, the memory 34 is configured to store a number of responses and associated patient and procedure characteristics relating to a number of post-operative patients. For example, each post-operative patient in a certain region or under the care of a certain facility or doctor may receive a health questionnaire, such as the CS questionnaire previously discussed, to complete at a predetermined time (e.g., six months after surgery). The post-operative patient may receive the questionnaire in the mail in hard copy form or electronically. For example, the patient may be instructed to visit a certain website to complete a response to the questionnaire on-line, or the patient may receive an electronic form of the questionnaire via e-mail. Thus, in some cases, the system 30 may include a display device 38 configured to present the health questionnaire to a user (e.g., the post-operative patient or medical personnel). The display device 38 may include, for example, a computer monitor or a display of a mobile terminal (such as a cell phone or PDA).

Regardless of the form of the questionnaire and response as completed by each post-operative patient, each response may eventually be received by the user input device 32. If the patient filled out a hard copy form of the questionnaire and mailed it back to a central location, such as the medical facility or processing center, users at the facility or center may input the response via the user input device 32. Likewise, if the patient receives an electronic form of the questionnaire, such as by completing a response on-line, the post-operative patient himself may enter the response using the user input device 32, which in this case may be a personal computer or a device associated with the computer, among other devices. For example, the user at the medical facility or the post-operative patient himself, depending on the form of the questionnaire, may use a terminal 14 such as terminal B shown in FIG. 7 to store a response in memory. In FIG. 7, as previously mentioned, the memory is in the form of a database 12.

Referring again to FIG. 9, the processor 36 may thus be configured to access the responses and associated characteristics from the memory 34, to analyze any response having at least one associated patient or procedure characteristic that matches a characteristic of the pre-operative patient, and to select the hernia repair procedure associated with the most matching responses having an overall score indicating the least effect of the hernia repair procedure on the respective post-operative patient's quality of life. Alternatively, the processor 36 may be configured to access the responses and associated characteristics from the memory 34, to identify at least one of the responses that has the greatest number of associated patient characteristics that match characteristics of the pre-operative patient, and to select the hernia repair procedure associated with the most identified responses having an overall score indicating the least effect of the hernia repair procedure on the respective post-operative patient's quality of life, as previously described in conjunction with the example illustrated in FIG. 8. Many other algorithms may be used by the processor to determine the hernia repair procedure (i.e., mesh type and/or operation type) for a pre-operative patient with certain characteristics, and these are provided only as examples. In some algorithms, for example, only responses having an overall score within a certain range, such as 0 to 30, may be considered.

As previously discussed, the health questionnaire may have several forms and may be structured in any way that elicits the relevant information from the post-operative patient. In some cases, the user input device 32, shown in FIG. 9, may be configured to receive a rating as the answer to each question included on the questionnaire. The rating may be indicative of the effect of the associated hernia repair procedure on the aspect of the post-operative patient's quality of life included in the respective question (for example, the severity of pain experienced when the patient is walking up stairs), and the overall score for the response may be a sum of the ratings. Thus, as mentioned above, a health questionnaire with 20 questions and an available rating of 0 to 5 for each question may have an overall score ranging from 0 to 100. Furthermore, in some cases, the processor may look to responses including only certain ratings, such as ratings less than 2 where a rating of 0 indicates no negative effects, when determining an optimum hernia repair procedure.

The processor 36 may be configured to execute a number of other program modules in addition to those described above. For example, another program module may display a questionnaire to a user, such as a post-operative patient or another user responding to the questionnaire, for example on behalf of a post-operative patient. The program module may display the questionnaire in various ways, such as all at once, allowing the user to jump from one question to the next, or one question at a time. Yet another program module may receive answers to the questions included in a particular quality of life questionnaire. The program module may, for example, receive a rating of 0 to 5 as an answer to each question of the questionnaire. Still another program module may compile the responses received to facilitate the determination of an optimum hernia repair procedure according to one or more statistical/analytical methods, and another program module may receive queries or search criteria to recall matching responses and/or answers from a database where the responses are stored.

The different components of the system 30 (e.g., the input device 32, the memory 34, and the processor 36) may be co-located, such as part of a single computer, or they may be distributed over a common network, for example on different computers connected to the same network. Thus, for example, one or more input devices 32 may be provided within a single medical facility or a number of medical facilities or at the homes of post-operative patients (e.g., on different computer terminals connected to the Internet) for receiving responses to a questionnaire. The memory 34, which may also be in a single location or distributed over several pieces of hardware connected to the network, may in turn store the responses such that the processor 36 may access the data and determine an optimum hernia repair procedure. In this way, post-operative patients and other users may be spread across a large geographic region but may still contribute to the pool of data stored in the memory 34, allowing for a more accurate statistical determination of the optimum procedure, as previously described.

Figure 10:
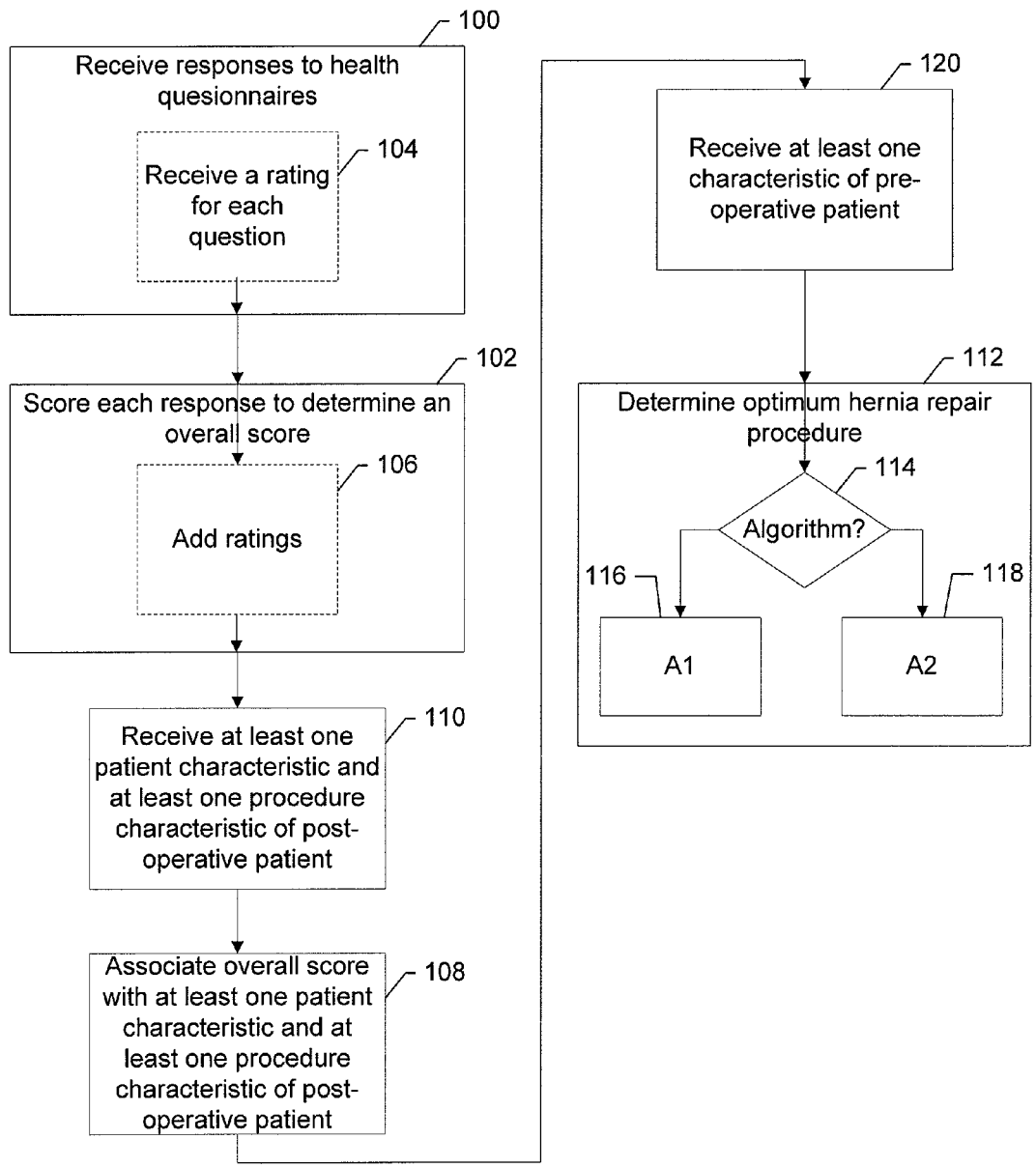
FIG. 10 illustrates a flowchart according to an exemplary embodiment for determining a hernia repair procedure for a pre-operative patient.

In other embodiments, a method for determining a hernia repair procedure for a pre-operative patient is provided. Referring to FIG. 10, responses to a number of health questionnaires administered to a number of patients who have previously undergone a hernia repair operation in which a prosthetic mesh was used to repair the hernia are received, for example via a user input device as previously described. Each health questionnaire, which may be a CS questionnaire, includes a number of questions, and each question relates to the effect of the hernia repair operation on an aspect of the post-operative patient's quality of life. Such aspects include the severity of pain, sensations of the mesh, and limitations in movement experienced by the post-operative patient in connection with performing at least five activities, such as lying down, bending over, sitting up, walking, exercising, walking up stairs, performing activities of daily life, coughing, and deep breathing. See FIG. 10, block 100.

Each response is then scored to determine an overall score for the response. Block 102. For example, and as previously described, a rating may be received as the answer to each question included on a particular questionnaire, and the ratings may be added to determine the overall score. Blocks 104, 106. The rating may be indicative of the effect of the associated hernia repair procedure on an aspect of the post-operative patient's quality of life included in the respective question. Thus, if a rating of 0 indicates that no symptoms are experienced (i.e., no negative impact on quality of life for the given aspect) and a rating of 5 indicates that disabling symptoms are experienced, and the questionnaire consists of 23 questions, an overall score of 22 may indicate a relatively small negative effect on quality of life based on the ratings whereas an overall score of 103 would indicate a relatively large negative effect on quality of life.

The overall score is then associated with at least one characteristic of the respective post-operative patient and with at least one characteristic of the hernia repair procedure performed. Block 108. The patient and procedure characteristics may already be stored in an accessible memory, such as a patient database or archive file. In some cases, the patient and procedure characteristics relating to the post-operative patient may be received, for example as part of the response to the questionnaire or as a supplemental input, as described above. Block 110. Patient characteristics may include the patient's age, gender, type of hernia, and pre-operative health, whereas procedure characteristics may include the type of operation performed and the type of prosthetic mesh used in the procedure.

An optimum hernia repair procedure for the pre-operative patient may be determined based on the overall scores and the associated characteristics. Block 112. The optimum procedure (i.e., the procedure likely to result in the smallest negative impact on the pre-operative patient's quality of life) may be determined according to many different algorithms and types of statistical analyses, as previously described. Thus, in some cases, there may be a choice of which algorithm to use for a particular determination. Blocks 114, 116, 118. For example, algorithm A1 may include analyzing a number of responses having at least one associated characteristic that matches a characteristic of the pre-operative patient and selecting the hernia repair procedure (i.e., type of operation and/or type of mesh) associated with the most matching responses having an overall score indicating the least effect of the hernia repair procedure on the respective post-operative patient's quality of life. Block 116.

Another algorithm, A2, may include identifying at least one of a number of responses that has the greatest number of associated characteristics that match characteristics of the pre-operative patient and selecting the hernia repair procedure associated with the identified responses having an overall score indicating the least effect of the hernia repair procedure on the respective post-operative patient's quality of life. Block 118. Although only two algorithms are shown in FIG. 10, numerous other algorithms may be used, as well as combinations of algorithms. For example, another algorithm may consider responses having a particular overall score, such as an overall score less than 20, while yet another algorithm may consider responses in which the answers are ratings less than 2.

In some cases, at least one characteristic relating to the pre-operative patient may be received, for example through input of one or more search criteria. Block 120. Such characteristics may include the patient's age, gender, type of hernia, pre-operative health, and/or type of operation recommended. Although the receipt of one or more characteristics of the pre-operative patient is shown as occurring after the overall score is associated with the patient and procedure characteristics of the post-operative patient, the characteristic(s) of the pre-operative patient may be received at any point and may be received simultaneously with the execution of other steps.

In other embodiments, a method of determining a hernia repair procedure for a pre-operative patient may include initially providing as a search criteria at least one characteristic relating to the pre-operative patient. The characteristic may include the patient's age, gender, type of hernia, pre-operative health, and/or type of operation recommended, among other characteristics. A database of responses to health questionnaires, such as the database 12 shown in FIG. 7, may then be queried to identify responses matching at least one of the search criteria provided. See FIG. 11, blocks 200, 202. As previously described, the health questionnaires (which may be CS questionnaires) were administered to a number of patients who have previously undergone a hernia repair operation in which a prosthetic mesh was used to repair the hernia. Furthermore, each health questionnaire may include a number of questions, and each question may relate to the effect of the hernia repair operation on an aspect of the post-operative patient's quality of life, such as the severity of pain, sensations of the prosthetic mesh, and limitations in movement experienced by the post-operative patient in connection with performing at least five activities. Such activities may include lying down, bending over, sitting up, walking, exercising, walking up stairs, performing activities of daily life, coughing, and deep breathing.

At least one output, including the optimum type of operation and/or the optimum type of prosthetic mesh to be used in the hernia repair procedure for the pre-operative patient, may then be received. Block 204. The output may be based on an analysis of the identified responses, where the analysis determines the output having the least effect on a post-operative patient having the greatest number of characteristics in common with the pre-operative patient. As previously described, the analysis may implement any of a number of algorithms and/or statistical methods.

In some cases, multiple characteristics relating to the pre-operative patient may be prioritized. In this way, identified responses matching characteristics having the highest priority may be considered more significant than identified responses matching characteristics having priorities less than the highest priority. Block 206. For example, certain characteristics, such as the pre-operative patient's pre-operative health and age, may be weighted greater than other characteristics, such as gender. In this case, responses matching the pre-operative patient's pre-operative health and age would be considered more significant than responses matching the pre-operative patient's gender, and the output would be determined accordingly.

Exemplary embodiments of the present invention have been described above with reference to block diagrams and flowchart illustrations of systems, methods, and computer program products. It will be understood that each block of the block diagrams and flowchart illustrations, and combinations of blocks in the block diagrams and flowchart illustrations, respectively, can be implemented by various means including computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

Figure 11:
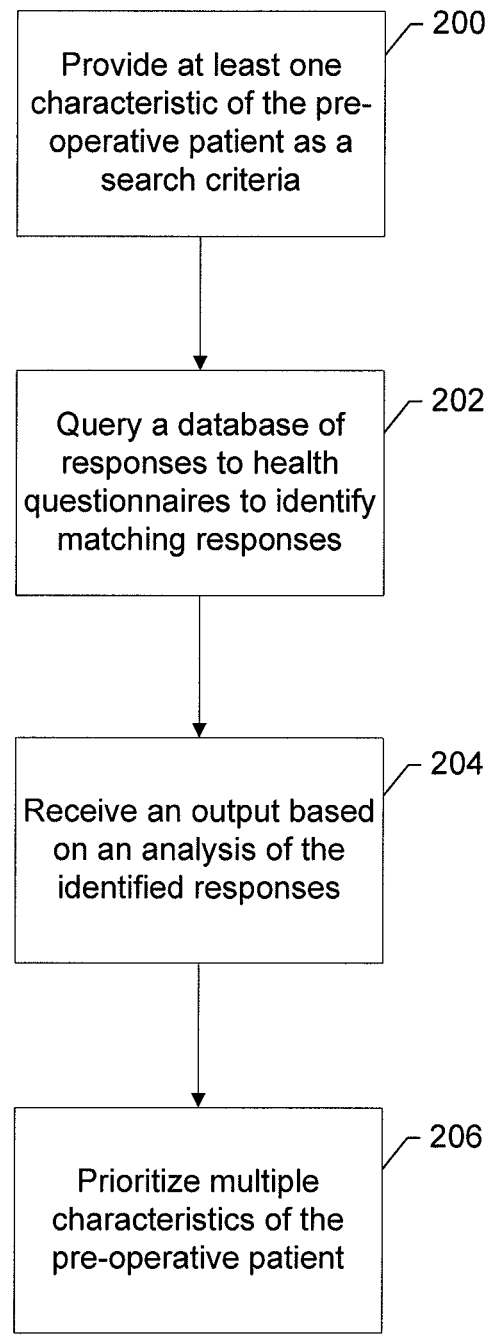
FIG. 11 illustrates a flowchart according to another exemplary embodiment for determining a hernia repair procedure for a pre-operative patient.

These computer program instructions may also be stored in a computer-readable memory that can direct a computer or other programmable data processing apparatus, such as the memory 34 shown in FIG. 9, to function in a particular manner, such that the instructions stored in the computer-readable memory produce an article of manufacture including computer-readable instructions for implementing the function specified in the flowchart block or blocks illustrated in FIGS. 10 and 11. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for determining a hernia repair procedure for a pre-operative hernia patient comprising:
a user input device configured to receive a response to a health questionnaire administered to a patient who has previously undergone a hernia repair procedure in which a prosthetic mesh was used to repair the hernia, wherein the health questionnaire includes a plurality of questions and each question relates to the effect of the hernia repair procedure on an aspect of the post-operative hernia patient's quality of life;
a memory configured to store data; and
a processor in communication with the user input device and the memory, wherein the processor is configured to execute:
a first program module operable for scoring the response to determine an overall score indicative of the respective post-operative hernia patient's quality of life based on severity of pain, sensations of the prosthetic mesh, and limitations in movement experienced by the post-operative hernia patient in connection with performing at least five activities selected from the group consisting of lying down, bending over, sitting up, walking, exercising, walking up stairs, performing activities of daily life, coughing, and deep breathing;
a second program module operable for associating the overall score with at least one characteristic of the respective post-operative hernia patient and with at least one characteristic of the respective hernia repair procedure performed; and
a third program module operable for determining an optimum hernia repair procedure for the pre-operative hernia patient based on the overall score and the associated patient characteristics.

2. The system of claim 1, wherein the user input device is configured to receive a rating as an answer to each question, wherein the rating is indicative of the effect of the associated hernia repair procedure on the aspect of the post-operative hernia patient's quality of life included in the respective question and wherein the overall score comprises a sum of the ratings.

3. The system of claim 1 further including a display device configured to present the health questionnaire a user.

4. The system of claim 1, wherein the user input device is configured to receive at least one hernia patient characteristic relating to the post-operative hernia patient selected from the group consisting of the hernia patient's age, gender, type of hernia, and pre-operative health and to receive at least one hernia repair procedure characteristic relating to the post-operative hernia patient selected from the group consisting of the type of hernia operation performed and the type of prosthetic mesh used in the procedure.

5. The system of claim 1, wherein the user input device is configured to receive at least one characteristic relating to the pre-operative hernia patient selected from the group consisting of the pre-operative hernia patient's age, gender, type of hernia, pre-operative health, and type of hernia operation recommended.

6. The system of claim 1, wherein the memory is configured to store a plurality of responses and associated hernia patient and hernia repair procedure characteristics relating to a plurality of post-operative hernia patients.

7. The system of claim 6, wherein the processor is configured to access the plurality of responses and associated characteristics from the memory, to analyze any response having at least one associated characteristic that matches a characteristic of the pre-operative hernia patient, and to select the hernia repair procedure associated with the most matching responses having an overall score indicating the least effect of the hernia repair procedure on the respective post-operative hernia patient's quality of life.

8. The system of claim 6, wherein the processor is configured to access the plurality of responses and associated characteristics from the memory, to identify at least one of the plurality of responses that has the greatest number of associated hernia patient characteristics that match characteristics of the pre-operative hernia patient, and to select the hernia repair procedure associated with the most identified responses having an overall score indicating the least effect of the hernia repair procedure on the respective post-operative hernia patient's quality of life.

9. The system of claim 1, wherein the third program module further comprises prioritizing multiple characteristics relating to the pre-operative hernia patient such that identified responses matching characteristics having the highest priority are considered more significant than identified responses matching characteristics having priorities less than the highest priority.

10. The system of claim 1, wherein only responses having an overall score within a desired range are considered in determining the hernia repair procedure for the pre-operative hernia patient.

11. A system for determining a hernia repair procedure for a pre-operative hernia patient comprising:
a memory configured to store a database of responses to a health questionnaire administered to a plurality of patients who have previously undergone a hernia repair procedure in which a prosthetic mesh was used to repair the hernia, wherein each response is associated with an overall score indicative of the effect of the hernia repair procedure on an aspect of the post-operative hernia patient's quality of life including severity of pain, sensations of the prosthetic mesh, and limitations in movement experienced by the post-operative hernia patient in connection with performing at least five activities selected from the group consisting of lying down, bending over, sitting up, walking, exercising, walking up stairs, performing activities of daily life, coughing, and deep breathing, and wherein each overall score is associated with at least one characteristic of the respective post-operative hernia patient and with at least one characteristic of the respective hernia repair procedure performed;
a terminal configured to receive search criteria comprising at least one characteristic relating to the pre-operative hernia patient selected from the group consisting of the pre-operative hernia patient's age, gender, type of hernia, pre-operative health, and type of hernia operation recommended; and
a server in communication with the database and the terminal, wherein the server is configured to query the database and to determine an optimum hernia repair procedure for the pre-operative hernia patient based on the overall scores, the associated hernia patient characteristics, and the search criteria received.

12. The system of claim 11, wherein the server is configured to analyze the responses in the database having at least one associated hernia patient characteristic that matches at least one characteristic included in the search criteria and to select the hernia repair procedure associated with the most matching responses having an overall score indicating the least effect of the hernia repair procedure on the respective post-operative hernia patient's quality of life.

13. The system of claim 11, wherein the server is configured to identify at least one of the responses in the database that has the greatest number of associated characteristics that match the search criteria and to select the hernia repair procedure associated with the identified responses having an overall score indicating the least effect of the hernia repair procedure on the respective post-operative hernia patient's quality of life.

14. The system of claim 11, wherein the server prioritizes multiple characteristics relating to the pre-operative hernia patient such that identified responses matching characteristics having the highest priority are considered more significant than identified responses matching characteristics having priorities less than the highest priority.

15. The system of claim 11, wherein only responses having an overall score within a desired range are considered in determining the hernia repair procedure for the pre-operative hernia patient.

16. A computer program product comprising at least one non-transitory computer-readable storage medium having computer-readable program code portions stored therein, the computer-readable program code portions comprising:
a first executable portion for receiving a plurality of responses to health questionnaires administered to a plurality of patients who have previously undergone a hernia repair procedure in which a prosthetic mesh was used to repair the hernia, wherein each health questionnaire includes a plurality of questions and each question relates to the effect of the hernia repair procedure on an aspect of the post-operative hernia patient's quality of life;
a second executable portion for scoring each response to determine an overall score indicative of a post-operative quality of life for each respective post-operative hernia patient based on severity of pain, sensations of the prosthetic mesh, and limitations in movement experienced by the post-operative hernia patient in connection with performing at least five activities selected from the group consisting of lying down, bending over, sitting up, walking, exercising, walking up stairs, performing activities of daily life, coughing, and deep breathing;
a third executable portion for associating each overall score with at least one characteristic of the respective post-operative hernia patient and with at least one characteristic of the respective hernia repair procedure performed; and
a fourth executable portion for determining an optimum hernia repair procedure for the pre-operative hernia patient based on the overall scores and the associated characteristics.

17. The computer program product of claim 16, wherein the first executable portion is further configured for receiving a rating as an answer to each question, wherein the rating is indicative of the effect of the associated hernia repair procedure on the aspect of the post-operative hernia patient's quality of life included in the respective question and wherein the second executable portion is further configured for adding the ratings to obtain the overall score.

18. The computer program product of claim 16, wherein the first executable portion is further configured for receiving at least one hernia patient characteristic relating to the post-operative hernia patient selected from the group consisting of the hernia patient's age, gender, type of hernia, and pre-operative health and for receiving at least one hernia repair procedure characteristic relating to the post-operative hernia patient selected from the group consisting of the type of hernia operation performed and the type of prosthetic mesh used in the procedure.

19. The computer program product of claim 16 further comprising a fifth executable portion for receiving search criteria comprising at least one characteristic relating to the pre-operative hernia patient selected from the group consisting of the pre-operative hernia patient's age, gender, type of hernia, pre-operative health, and type of hernia operation recommended and identifying responses that include the search criteria.

20. The computer program product of claim 16, wherein the fourth executable portion further comprises analyzing a plurality of responses having at least one associated characteristic that matches a characteristic of the pre-operative hernia patient and selecting the hernia repair procedure associated with the most matching responses having an overall score indicating the least effect of the hernia repair procedure on the respective post-operative hernia patient's quality of life.

21. The computer program product of claim 16, wherein the fourth executable portion further comprises identifying at least one of the plurality of responses that has the greatest number of associated characteristics that match characteristics of the pre-operative hernia patient and selecting the hernia repair procedure associated with the identified responses having an overall score indicating the least effect of the hernia repair procedure on the respective post-operative hernia patient's quality of life.

22. The computer program product of claim 16, wherein the fourth executable portion further comprises prioritizing multiple characteristics relating to the pre-operative hernia patient such that identified responses matching characteristics having the highest priority are considered more significant than identified responses matching characteristics having priorities less than the highest priority.

23. The computer program product of claim 16, wherein only responses having an overall score within a desired range are considered in determining the hernia repair procedure for the pre-operative hernia patient.

24. A method of determining a hernia repair procedure for a pre-operative hernia patient comprising:
provinding as a search criteria to a computer system at least one characteristic relating to the pre-operative hernia patient selected from the group consisting of the pre-operative hernia patient's age, gender, type of hernia, pre-operative health, and type of hernia operation recommended;
querying a database stored in a memory, the database including responses to health questionnaires to identify responses matching at least one of the search criteria provided, wherein the health questionnaires were administered to a plurality of patients who have previously undergone a hernia repair procedure in which a prosthetic mesh was used to repair the hernia, and wherein each health questionnaire includes a plurality of questions and each question relates to the effect of the hernia repair procedure on an aspect of the post-operative hernia patient's quality of life; and
determining, via a processor, at least one output selected from the group consisting of an optimum type of hernia operation and an optimum type of prosthetic mesh to be used in the hernia repair procedure for the pre-operative hernia patient based on an association between an overall score with at least one characteristic of a post-operative hernia patient and with at least one characteristic of the respective hernia repair procedure performed, wherein the overall score is indicative of the respective post-operative hernia patient quality of life based on severity of pain, sensations of the prosthetic mesh, and limitations in movement experienced by the post-operative hernia patient in connection with performing at least five activities selected from the group consisting of lying down, bending over, sitting up, walking, exercising, walking up stairs, performing activities of daily life, coughing, and deep breathing.

25. The method of claim 24 further comprising prioritizing multiple characteristics relating to the pre-operative hernia patient such that identified responses matching characteristics having the highest priority are considered more significant than identified responses matching characteristics having priorities less than the highest priority.

* * * * *